(12) United States Patent
Lund et al.

(10) Patent No.: US 11,234,446 B2
(45) Date of Patent: Feb. 1, 2022

(54) STABILIZATION OF CHYMOSIN BY POLYMERS

(71) Applicant: Chr. Hansen A/S, Hoersholm (DK)

(72) Inventors: Martin Lund, Copenhagen Ø (DK); Jonas Jacobsen, Copenhagen Ø (DK); Johannes Maarten Van Den Brink, Herlev (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

(21) Appl. No.: 17/024,112

(22) Filed: Sep. 17, 2020

(65) Prior Publication Data

US 2021/0045401 A1 Feb. 18, 2021

Related U.S. Application Data

(62) Division of application No. 14/902,946, filed as application No. PCT/EP2014/064913 on Jul. 11, 2014, now Pat. No. 10,779,552.

(30) Foreign Application Priority Data

Jul. 18, 2013 (EP) .................................... 13177064

(51) Int. Cl.
*C12N 9/64* (2006.01)
*A23C 19/032* (2006.01)

(52) U.S. Cl.
CPC .......... *A23C 19/032* (2013.01); *C12N 9/6478* (2013.01); *C12N 9/6481* (2013.01); *C12N 9/6483* (2013.01); *C12Y 304/23004* (2013.01)

(58) Field of Classification Search
CPC .................................................. C12N 9/6483
USPC ....................................................... 435/212
See application file for complete search history.

(56) References Cited

U.S. PATENT DOCUMENTS

| 3,798,128 | A | 3/1974 | Minato et al. |
| 4,233,405 | A | 11/1980 | Neubeck |
| 5,139,943 | A | 8/1992 | Heinsohn et al. |
| 7,998,705 | B2 | 8/2011 | Wan et al. |
| 10,779,552 | B2 * | 9/2020 | Lund .................... C12N 9/6478 |
| 2011/0008846 | A1 | 1/2011 | Heinsohn et al. |

FOREIGN PATENT DOCUMENTS

| DE | 14 92 060 A1 | 3/1969 |
| EP | 2 333 056 A1 | 6/2011 |
| WO | WO-90/15866 A1 | 12/1990 |
| WO | WO-02/36752 A2 | 5/2002 |
| WO | WO-2007/118838 A1 | 10/2007 |
| WO | WO-2008/091740 A2 | 7/2008 |
| WO | WO-2012/127005 A1 | 9/2012 |

OTHER PUBLICATIONS

Kappeler et al., "Characterization of recombinant camel chymosin reveals superior properties for the coagulation of bovine and camel milk," Biochemical and Biophysical Research Communications 342 (2006) 647-654.
PCT International Search Report issued in application PCT/EP2014/064913 dated Oct. 15, 2014; 5 pages.
Spelzini et al. "Features of the acid protease partition in aqueous two-phase systems of polyethylene glycol-phosphate: Chymosin and pepsin," Journal of Chromatography B, vol. 821, pp. 60-66 (2005) (Available online May 2005).
Ellaiah et al., "A Review on Microbial Alkaline Proteases," Journ. of Scientific & Industrial Research, vol. 61, pp. 690-704 (Sep. 2002).
Friedenthal et al., "Enzyme Adsorption and Loss of Activity in Dilute Solutions of Chymosin and Pepsin. Prevention with Polyethylene Glycol," Netherlands Milk and Dairy Journal, vol. 39, pp. 63-70 (1985).
GenBank Acc# CAC19554.1 from Kappeler et al., "Biochemical and Biophysical Research Communications," 342 (2006) 647-654. Alignment with SID 5.
Jensen et al., "Camel and bovine chymosin: the relationship between their structures and cheesemaking properties." Apr. 19, 2013; Acta. Cryst. (2013), D69, 901-913.

\* cited by examiner

*Primary Examiner* — Sheridan Swope
(74) *Attorney, Agent, or Firm* — Foley & Lardner LLP

(57) ABSTRACT

A liquid or dried granulated milk clotting aspartic protease enzyme composition and process for isolating a milk clotting aspartic protease enzyme of interest.

8 Claims, 7 Drawing Sheets

Figure 3:
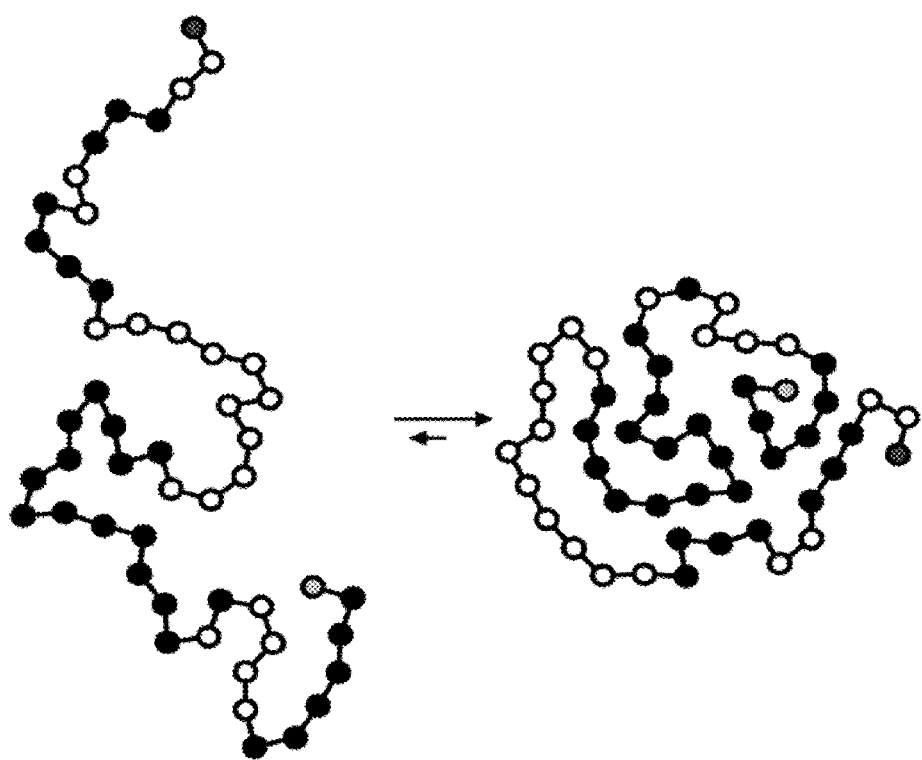

Specification includes a Sequence Listing.

Figure 1
PEG
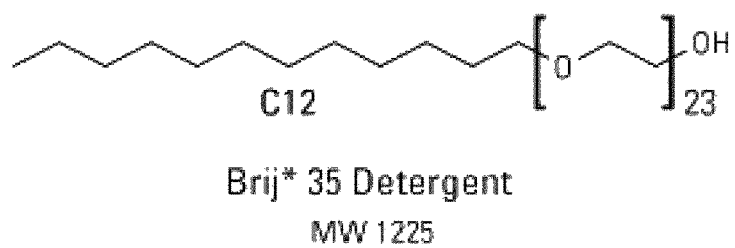
Brij* 35 Detergent
MW 1225

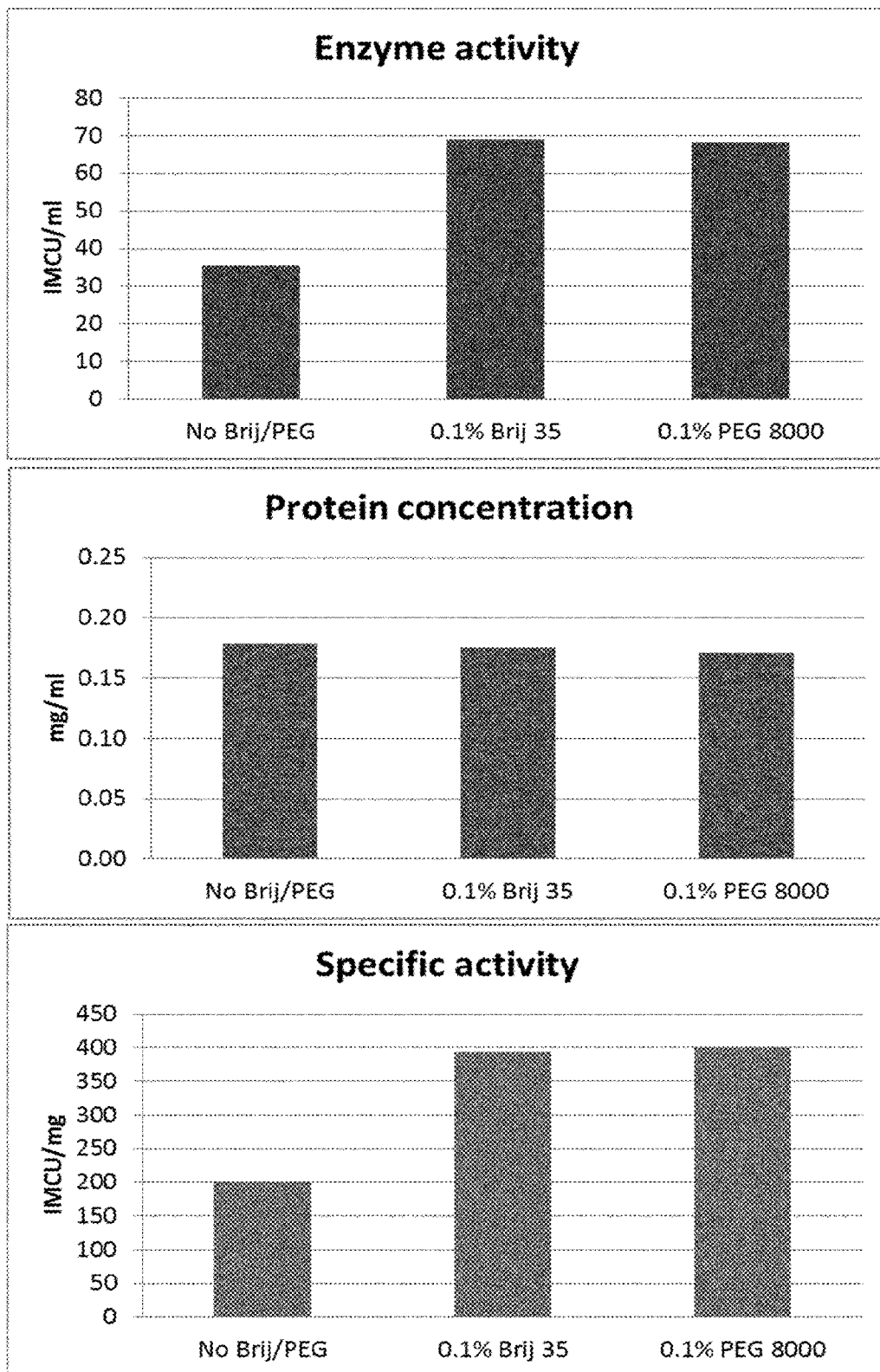
Figure 2A: Camel chymosin

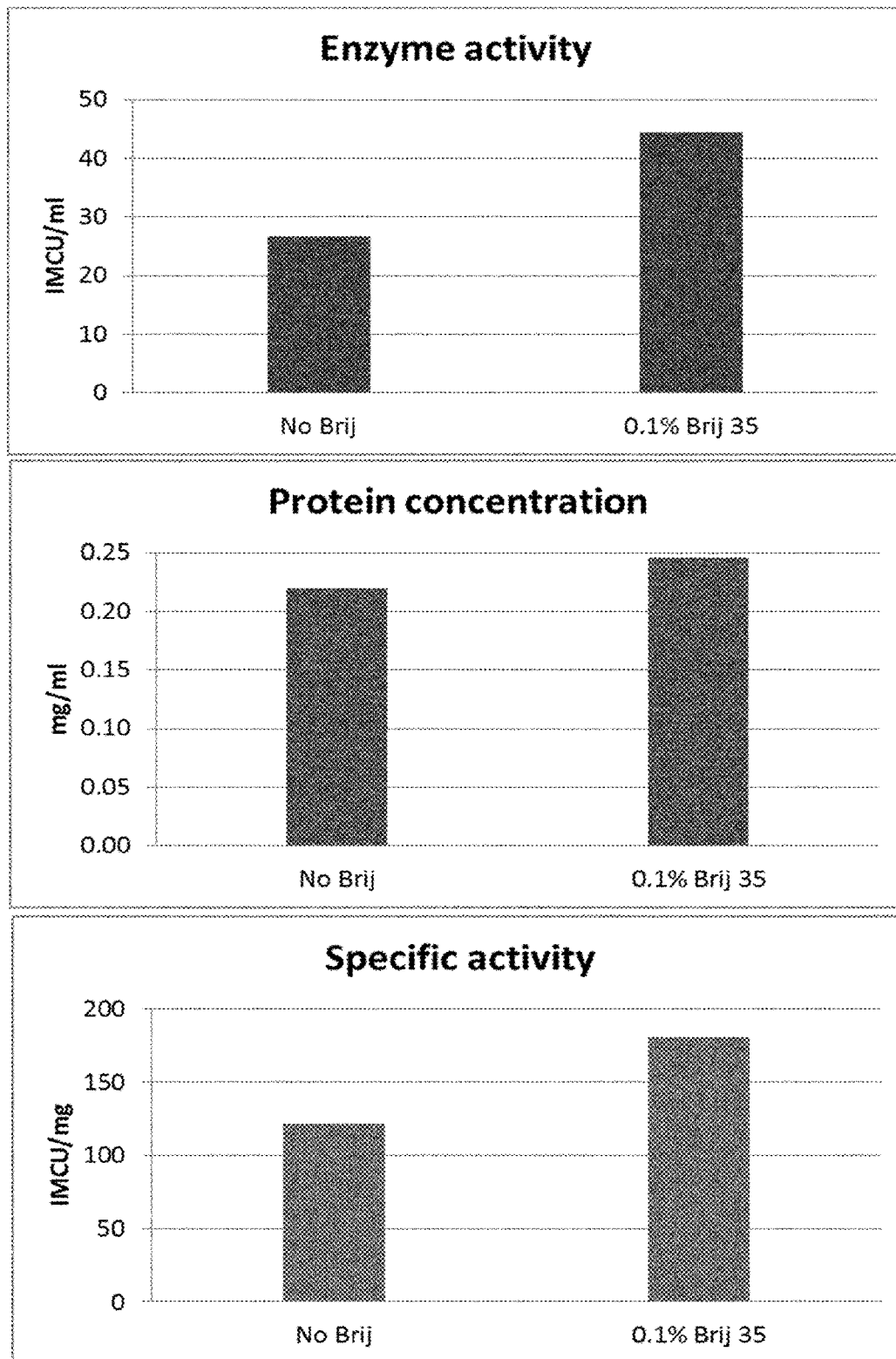
Figure 2B: Bovine chymosin

Figure 4

```
Cow        GEVASVPLTNYLDSQYFGKIYLGTPPQEFTVLFDTGSSDFWVPSIYCKSNACKNHQRFDP
Buffalo    GEVASVPLTNYLDSQYFGKIYLGTPPQEFTVLFDTGSSDFWVPSIYCKSNACKNHQRFDP
Goat       GEVASVPLTNYLDSQYFGKIYLGTPPQEFTVLFDTGSSDFWVPSIYCKSNACKNHQRFDP
Sheep      GEVASVPLTNYLDSQYFGKIYLGTPPQEFTVLFDTGSSDFWVPSIYCKSNACKNHQRFDP
Camel      GKVAREPLTSYLDSQYFGKIYIGTPPQEFTVVFDTGSSDLWVPSIYCKSNVCKNHHRFDP
Pig        GEVASEPLTNYLDTQYFGKIYIGTPPQEFTVVFDTGSSELWVPSVYCKSDACQNHHRFNP
           *:**   ***.***:*******:**********:*****::****:****:..*:**:**:*

Cow        RKSSTFQNLGKPLSIHYGTGSMQGILGYDTVTVSNIVDIQQTVGLSTQEPGDVFTYAEFD
Buffalo    RKSSTFQNLGKPLSIRYGTGSMQGILGYDTVTVSNIVDIQQTVGLSTQEPGDVFTYAEFD
Goat       RKSSTFQNLGKPLSIRYGTGSMQGILGYDTVTVSNIVDTQQTVGLSTQEPGDVFTYAEFD
Sheep      RKSSTFQNLGKPLSIRYGTGSMQGILGYDTVTVSNIVDIQQTVGLSTQEPGDVFTYAEFD
Camel      RKSSTFRNLGKPLSIHYGTGSMEGFLGYDTVTVSNIVDPNQTVGLSTEQPGEVFTYSEFD
Pig        SKSSTFQNLDKPLSIQYGTGSIQGFLGYDTVMVAGIVDAHQTVGLSTQEPSDIFTYSEFD
           ****:**.*****:*****::*:****** *:.***  :*******::*.::***:***

Cow        GILGMAYPSLASEYSIPVFDNMMNRHLVAQDLFSVYMDRNGQESMLTLGAIDPSYYTGSL
Buffalo    GILGMAYPSLASEYSIPVFDNMMNRHLVAQDLFSVYMDRNGQESMLTLGAIDPSYYTGSL
Goat       GILGMAYPSLASEYSVPVFDNMMDRRLVAQDLFSVYMDRNGQGSMLTLGAIDPSYYTGSL
Sheep      GILGMAYPSLASEYSVPVFDNMMDRRLVAQDLFSVYMDRSGQGSMLTLGAIDPSYYTGSL
Camel      GILGLAYPSLASEYSVPVFDNMMDRHLVARDLFSVYMDRNGQGSMLTLGAIDPSYYTGSL
Pig        GILGLGYPELASEYTVPVFDNMMHRHLVAQDLFAVYMSRNDEGSMLTLGAIDPSYYTGSL
           ****:.**.*****::******.*:***:***.*** ..: *****************

Cow        HWVPVTVQQYWQFTVDSVTISGVVVACEGGCQAILDTGTSKLVGPSSDILNIQQAIGATQ
Buffalo    HWVPVTVQQYWQFTVDSITISGVVVACEGGCQAILDTGTSKLVGPSSDILNIQQAIGATQ
Goat       HWVPVTLQKYWQFTVDSVTISGAVVACEGGCQAILDTGTSKLVGPSSDILNIQQAIGATQ
Sheep      HWVPVTLQKYWQFTVDSVTISGAVVACEGGCQAILDTGTSKLVGPSSDILNIQQAIGATQ
Camel      HWVPVTLQQYWQFTVDSVTINGVAVACVGGCQAILDTGTSVLFGPSSDILKIQMAIGATE
Pig        HWVPVTMQLYWQFTVDSVTINGVVVACNGGCQAILDTGTSMLAGPSSDILNIQMAIGATE
           ******:* ********:** *.*** ************ *.*******:** *****:

Cow        NQYGEFDIDCDNLSYMPTVVFEINGKMYPLTPSAYTSQDQGFCTSGFQSENHSQKWILGD
Buffalo    NQYGEFDIDCDNLSYMPTVVFEINGKMYPLTPSAYTSQDQGFCTSGFQSENRSQQWILGD
Goat       NQYGEFDIDCDSLSSMPTVVFEINGKMYPLTPYAYTSQEEGFCTSGFQGENHSHQWILGD
Sheep      NQYGEFDIDCDSLSSMPTVVFEINGKMYPLTPYAYTSQEEGFCTSGFQGENHSHQWILGD
Camel      NRYGEFDVNCGNLRSMPTVVFEINGRDYPLSPSAYTSKDQGFCTSGFQGDNNSELWILGD
Pig        SQYGEFDIDCGSLSSMPTVVFEISGRMYPLPPSAYTNQDQGFCTSGFQGDSKSQHWILGV
           .:*****::.**  ********.*: ***.* ***.:::*******.:...*. ****

Cow        VFIREYYSVFDRANNLVGLAKAI
Buffalo    VFIREYYSVFDRANNLVGLAKAI
Goat       VFIREYYSVFDRANNLVGLAKAI
Sheep      VFIREYYSVFDRANNLVGLAKAI
Camel      VFIREYYSVFDRANNRVGLAKAI
Pig        VFIQEYYSVFDRANNRVGLAKAI
           ***:*********** *******
```

Figure 5

```
Camel_chymosin   ----GKVAREPLTSYLDSQYFGKIYIGTPPQEFTVVFDTGSSDLWVPSIYCK-SNVCKNH
Cow_chymosin     ----GEVASVPLTNYLDSQYFGKIYLGTPPQEFTVLFDTGSSDFWVPSIYCK-SNACKNH
Cow_pepsin       --AATLVSEQPLQNYLDTEYFGTIGIGTPAQDFTVIFDTGSSNLWVPSIYCS-SEACTNH
Mucor            AAADGSVDTPGYYDFDLEEYAIPVSIGTPGQDFLLLFDTGSSDTWVPHKGCTKSEGCVGS
Endothia         ---STGSATTTPIDSLDDAYITPVQIGTPAQTLNLDFDTGSSDLWVFSSETT-ASEVDGQ
                    .     *   : :***  *  : : ******: **    . :.  .

Camel_chymosin   HRFDPRKSSTFRNLG-KPLSIHYGTG-SMEGFLGYDTVTVSNIVDPNQTVGLSTEQPGEV
Cow_chymosin     QRFDPRKSSTFQNLG-KPLSIHYGTG-SMQGILGYDTVTVSNIVDIQQTVGLSTQEPGDV
Cow_pepsin       NRFNPQDSSTYEATS-ETLSITYGTG-SMTGILGYDTVQVGGISDTNQIFGLSETEPGSF
Mucor            RFFDPSASSTFKATN-YNLNITYGTG-GANGLYFEDSIAIGDITVTKQILAYVDNVRGPT
Endothia         TIYTPSKSTTAKLLSGATWSISYGDGSSSSGDVYTDTVSVGGLTVTGQAVESAKKVSSSF
                  : *  *:*   .    .* ** * .  *   *:: :..:    *  .       .

Camel_chymosin   FTYSE------FDGILGLAYPS---LASEY---SVPVFDNMMDRHLVARDLFSVYMDRNGQ
Cow_chymosin     FTYAE------FDGILGMAYPS---LASEY---SIPVFDNMMNRHLVAQDLFSVYMDRNGQ
Cow_pepsin       LYYAP------FDGILGLAYPS---ISSSG----ATPVFDNIWDQGLVSQDLFSVYLSSNEE
Mucor            AEQSPNADIFLDGLFGAAYPDNTAMEAEYGSTYNTVHVNLYKQGLISSPLFSVYMNTNSG
Endothia         TEDST------IDGLLGLAFST---LNTVSPTQQKTFFDNAKAS--LDSPVFTADLGYHAP
                    :       :**::* *:.    : :       ...  *     :   :*:. :. :

Camel_chymosin   -GSMLTLGAIDPSYYTGSLHWVPVTLQQ----YWQFTVDSVTING-VAVACVGGCQAILD
Cow_chymosin     -ESMLTLGAIDPSYYTGSLHWVPVTVQQ----YWQFTVDSVTISG-VVVACEGGCQAILD
Cow_pepsin       SGSVVIFGDIDSSYYSGSLNWVPVSVEG----YWQITVDSITMNG-ESIACSDGCQAIVD
Mucor            -TGEVVFGGVNNTLLGGDIAYTDVMSRYGGYYFWDAPVTGITVDGSAAVRFSRPQAFTID
Endothia         --GTYNFGFIDTTAYTGSITYTAVSTKQG---FWEWTSTGYAVGS--GTFKSTSIDGIAD
                   .  :* :: :   *.: :. *  .    :*: .  .::..                *

Camel_chymosin   TGTSVLFGPSSDILKIQMAIG--ATENRYGEFDVNCGNLRSMPTVVFEINGRDYPLSPSA
Cow_chymosin     TGTSKLVGPSSDILNIQQAIG--ATQNQYGEFDIDCDNLSYMPTVVFEINGKMYPLTPSA
Cow_pepsin       TGTSLLAGPTTAISNIQSYIG--ASEDSSGEVVISCSSIDSLPDIVFTINGVQYPVPPSA
Mucor            TGTNFFIMPSSAASKIVKAALPDATETQQGWVVPCASYQNSKSTISIVMQKSGSSSDTIE
Endothia         TGTTLLYLPATVVSAYWAQVSGAKSSSSVGGYVFPCS--ATLPSFTFGVGSARIVIPGDY
                 ***. :   *::          :.   *    ..     . . : :

Camel_chymosin   YTS-KDQGFCTSGFQ---------GDNNSELWILGDVFIREYYSVFDRANN-RVGLAKAI
Cow_chymosin     YTS-QDQGFCTSGFQ---------SENHSQKWILGDVFIREYYSVFDRANN-LVGLAKAI
Cow_pepsin       YIL-QSNGICSSGFEG-----MDISTSSGDLWILGDVFIRQYFTVFDRGNN-QIGLAPVA
Mucor            ISV-PVSKMLLPVDQSNETCMFIILPDGGNQYIVGNLFLRFFVNVYDFGNN-RIGFAPLA
Endothia         IDFGPISTGSSSCFGG------IQSSAGIGINIFGDVALKAAFVVFNGATTPTLGFASK-
                               *.*:: ::    *:: ... :*:*

Camel_chymosin   ------
Cow_chymosin     ------
Cow_pepsin       ------
Mucor            SAYENE
Endothia         ------
```

Polysorbate 20

SEQUENCE LISTING

<160> NUMBER OF SEQ ID NOS: 9

<210> SEQ ID NO 1
<211> LENGTH: 323
<212> TYPE: PRT
<213> ORGANISM: Bos taurus

<400> SEQUENCE: 1

```
Gly Glu Val Ala Ser Val Pro Leu Thr Asn Tyr Leu Asp Ser Gln Tyr
1               5                   10                  15

Phe Gly Lys Ile Tyr Leu Gly Thr Pro Pro Gln Glu Phe Thr Val Leu
            20                  25                  30

Phe Asp Thr Gly Ser Ser Asp Phe Trp Val Pro Ser Ile Tyr Cys Lys
                35                  40                  45

Ser Asn Ala Cys Lys Asn His Gln Arg Phe Asp Pro Arg Lys Ser Ser
    50                  55                  60

Thr Phe Gln Asn Leu Gly Lys Pro Leu Ser Ile His Tyr Gly Thr Gly
65                  70                  75                  80

Ser Met Gln Gly Ile Leu Gly Tyr Asp Thr Val Thr Val Ser Asn Ile
                85                  90                  95

Val Asp Ile Gln Gln Thr Val Gly Leu Ser Thr Gln Glu Pro Gly Asp
                100                 105                 110

Val Phe Thr Tyr Ala Glu Phe Asp Gly Ile Leu Gly Met Ala Tyr Pro
                115                 120                 125

Ser Leu Ala Ser Glu Tyr Ser Ile Pro Val Phe Asp Asn Met Met Asn
        130                 135                 140

Arg His Leu Val Ala Gln Asp Leu Phe Ser Val Tyr Met Asp Arg Asn
145                 150                 155                 160

Gly Gln Glu Ser Met Leu Thr Leu Gly Ala Ile Asp Pro Ser Tyr Tyr
                165                 170                 175

Thr Gly Ser Leu His Trp Val Pro Val Thr Val Gln Gln Tyr Trp Gln
                180                 185                 190

Phe Thr Val Asp Ser Val Thr Ile Ser Gly Val Val Ala Cys Glu
                195                 200                 205

Gly Gly Cys Gln Ala Ile Leu Asp Thr Gly Thr Ser Lys Leu Val Gly
        210                 215                 220

Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Asn Leu Ser Tyr Met
                245                 250                 255

Pro Thr Val Val Phe Glu Ile Asn Gly Lys Met Tyr Pro Leu Thr Pro
                260                 265                 270

Ser Ala Tyr Thr Ser Gln Asp Gln Gly Phe Cys Thr Ser Gly Phe Gln
                275                 280                 285

Ser Glu Asn His Ser Gln Lys Trp Ile Leu Gly Asp Val Phe Ile Arg
        290                 295                 300

Glu Tyr Tyr Ser Val Phe Asp Arg Ala Asn Asn Leu Val Gly Leu Ala
305                 310                 315                 320

Lys Ala Ile

<210> SEQ ID NO 2
<211> LENGTH: 323
<212> TYPE: PRT
<213> ORGANISM: Unknown
<220> FEATURE:
<223> OTHER INFORMATION: Description of Unknown:
      Buffalo polypeptide

<400> SEQUENCE: 2

Gly Glu Val Ala Ser Val Pro Leu Thr Asn Tyr Leu Asp Ser Gln Tyr
1               5                   10                  15

Phe Gly Lys Ile Tyr Leu Gly Thr Pro Pro Gln Glu Phe Thr Val Leu
            20                  25                  30
```

-continued

Phe Asp Thr Gly Ser Ser Asp Phe Trp Val Pro Ser Ile Tyr Cys Lys
            35                  40                  45

Ser Asn Ala Cys Lys Asn His Gln Arg Phe Asp Pro Arg Lys Ser Ser
 50                  55                  60

Thr Phe Gln Asn Leu Gly Lys Pro Leu Ser Ile Arg Tyr Gly Thr Gly
 65                  70                  75                  80

Ser Met Gln Gly Ile Leu Gly Tyr Asp Thr Val Thr Val Ser Asn Ile
                    85                  90                  95

Val Asp Ile Gln Gln Thr Val Gly Leu Ser Thr Gln Glu Pro Gly Asp
                100                 105                 110

Val Phe Thr Tyr Ala Glu Phe Asp Gly Ile Leu Gly Met Ala Tyr Pro
                115                 120                 125

Ser Leu Ala Ser Glu Tyr Ser Ile Pro Val Phe Asp Asn Met Met Asn
130                 135                 140

Arg His Leu Val Ala Gln Asp Leu Phe Ser Val Tyr Met Asp Arg Asn
145                 150                 155                 160

Gly Gln Glu Ser Met Leu Thr Leu Gly Ala Ile Asp Pro Ser Tyr Tyr
                    165                 170                 175

Thr Gly Ser Leu His Trp Val Pro Val Thr Val Gln Gln Tyr Trp Gln
                180                 185                 190

Phe Thr Val Asp Ser Ile Thr Ile Ser Gly Val Val Ala Cys Glu
                195                 200                 205

Gly Gly Cys Gln Ala Ile Leu Asp Thr Gly Thr Ser Lys Leu Val Gly
                210                 215                 220

Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Asn Leu Ser Tyr Met
                    245                 250                 255

Pro Thr Val Val Phe Glu Ile Asn Gly Lys Met Tyr Pro Leu Thr Pro
                260                 265                 270

Ser Ala Tyr Thr Ser Gln Asp Gln Gly Phe Cys Thr Ser Gly Phe Gln
                275                 280                 285

Ser Glu Asn Arg Ser Gln Gln Trp Ile Leu Gly Asp Val Phe Ile Arg
290                 295                 300

Glu Tyr Tyr Ser Val Phe Asp Arg Ala Asn Asn Leu Val Gly Leu Ala
305                 310                 315                 320

Lys Ala Ile

<210> SEQ ID NO 3
<211> LENGTH: 323
<212> TYPE: PRT
<213> ORGANISM: Capra hircus

<400> SEQUENCE: 3

Gly Glu Val Ala Ser Val Pro Leu Thr Asn Tyr Leu Asp Ser Gln Tyr
1                5                  10                  15

Phe Gly Lys Ile Tyr Leu Gly Thr Pro Pro Gln Glu Phe Thr Val Leu
                    20                  25                  30

Phe Asp Thr Gly Ser Ser Asp Phe Trp Val Pro Ser Ile Tyr Cys Lys
                    35                  40                  45

Ser Asn Ala Cys Lys Asn His Gln Arg Phe Asp Pro Arg Lys Ser Ser
 50                  55                  60

Thr Phe Gln Asn Leu Gly Lys Pro Leu Ser Ile Arg Tyr Gly Thr Gly
 65                  70                  75                  80

Ser Met Gln Gly Ile Leu Gly Tyr Asp Thr Val Thr Val Ser Asn Ile
                85                  90                  95

Val Asp Thr Gln Gln Thr Val Gly Leu Ser Thr Gln Glu Pro Gly Asp
            100                 105                 110

Val Phe Thr Tyr Ala Glu Phe Asp Gly Ile Leu Gly Met Ala Tyr Pro
            115                 120                 125

Ser Leu Ala Ser Glu Tyr Ser Val Pro Val Phe Asp Asn Met Met Asp
130                 135                 140

Arg Arg Leu Val Ala Gln Asp Leu Phe Ser Val Tyr Met Asp Arg Asn
145                 150                 155                 160

Gly Gln Gly Ser Met Leu Thr Leu Gly Ala Ile Asp Pro Ser Tyr Tyr
                165                 170                 175

Thr Gly Ser Leu His Trp Val Pro Val Thr Leu Gln Lys Tyr Trp Gln
            180                 185                 190

Phe Thr Val Asp Ser Val Thr Ile Ser Gly Ala Val Val Ala Cys Glu
            195                 200                 205

Gly Gly Cys Gln Ala Ile Leu Asp Thr Gly Thr Ser Lys Leu Val Gly
            210                 215                 220

Pro Ser Ser Asp Ile Leu Asn Ile Gln Gln Ala Ile Gly Ala Thr Gln
225                 230                 235                 240

Asn Gln Tyr Gly Glu Phe Asp Ile Asp Cys Asp Ser Leu Ser Ser Met
                245                 250                 255

Pro Thr Val Val Phe Glu Ile Asn Gly Lys Met Tyr Pro Leu Thr Pro
            260                 265                 270

Tyr Ala Tyr Thr Ser Gln Glu Glu Gly Phe Cys Thr Ser Gly Phe Gln
            275                 280                 285

Gly Glu Asn His Ser His Gln Trp Ile Leu Gly Asp Val Phe Ile Arg
            290                 295                 300

Glu Tyr Tyr Ser Val Phe Asp Arg Ala Asn Asn Leu Val Gly Leu Ala
305                 310                 315                 320

Lys Ala Ile

<210> SEQ ID NO 4
<211> LENGTH: 323
<212> TYPE: PRT
<213> ORGANISM: Ovis aries

<400> SEQUENCE: 4

Gly Glu Val Ala Ser Val Pro Leu Thr Asn Tyr Leu Asp Ser Gln Tyr
1               5                   10                  15

Phe Gly Lys Ile Tyr Leu Gly Thr Pro Pro Gln Glu Phe Thr Val Leu
            20                  25                  30

Phe Asp Thr Gly Ser Ser Asp Phe Trp Val Pro Ser Ile Tyr Cys Lys
        35                  40                  45

Ser Asn Ala Cys Lys Asn His Gln Arg Phe Asp Pro Arg Lys Ser Ser
50                  55                  60

Thr Phe Gln Asn Leu Gly Lys Pro Leu Ser Ile Arg Tyr Gly Thr Gly
65                  70                  75                  80

Ser Met Gln Gly Ile Leu Gly Tyr Asp Thr Val Thr Val Ser Asn Ile
                85                  90                  95

Val Asp Ile Gln Gln Thr Val Gly Leu Ser Thr Gln Glu Pro Gly Asp
            100                 105                 110

Val Phe Thr Tyr Ala Glu Phe Asp Gly Ile Leu Gly Met Ala Tyr Pro
            115                 120                 125

```
Ser Leu Ala Ser Glu Tyr Ser Val Pro Val Phe Asp Asn Met Met Asp
        130                 135                 140

Arg Arg Leu Val Ala Gln Asp Leu Phe Ser Val Tyr Met Asp Arg Ser
145                 150                 155                 160

Gly Gln Gly Ser Met Leu Thr Leu Gly Ala Ile Asp Pro Ser Tyr Tyr
                165                 170                 175

Thr Gly Ser Leu His Trp Val Pro Val Thr Leu Gln Lys Tyr Trp Gln
            180                 185                 190

Phe Thr Val Asp Ser Val Thr Ile Ser Gly Ala Val Ala Cys Glu
                195                 200                 205

Gly Gly Cys Gln Ala Ile Leu Asp Thr Gly Thr Ser Lys Leu Val Gly
        210                 215                 220

Pro Ser Asp Ile Leu Asn Ile Gln Gln Ala Ile Gly Ala Thr Gln
225                 230                 235                 240

Asn Gln Tyr Gly Glu Phe Asp Ile Asp Cys Asp Ser Leu Ser Ser Met
                    245                 250                 255

Pro Thr Val Val Phe Glu Ile Asn Gly Lys Met Tyr Pro Leu Thr Pro
                260                 265                 270

Tyr Ala Tyr Thr Ser Gln Glu Glu Gly Phe Cys Thr Ser Gly Phe Gln
        275                 280                 285

Gly Glu Asn His Ser His Gln Trp Ile Leu Gly Asp Val Phe Ile Arg
    290                 295                 300

Glu Tyr Tyr Ser Val Phe Asp Arg Ala Asn Asn Leu Val Gly Leu Ala
305                 310                 315                 320

Lys Ala Ile

<210> SEQ ID NO 5
<211> LENGTH: 323
<212> TYPE: PRT
<213> ORGANISM: Camelus dromedarius

<400> SEQUENCE: 5

Gly Lys Val Ala Arg Glu Pro Leu Thr Ser Tyr Leu Asp Ser Gln Tyr
1               5                   10                  15

Phe Gly Lys Ile Tyr Ile Gly Thr Pro Pro Gln Glu Phe Thr Val Val
                20                  25                  30

Phe Asp Thr Gly Ser Ser Asp Leu Trp Val Pro Ser Ile Tyr Cys Lys
            35                  40                  45

Ser Asn Val Cys Lys Asn His His Arg Phe Asp Pro Arg Lys Ser Ser
    50                  55                  60

Thr Phe Arg Asn Leu Gly Lys Pro Leu Ser Ile His Tyr Gly Thr Gly
65                  70                  75                  80

Ser Met Glu Gly Phe Leu Gly Tyr Asp Thr Val Thr Val Ser Asn Ile
                85                  90                  95

Val Asp Pro Asn Gln Thr Val Gly Leu Ser Thr Glu Gln Pro Gly Glu
            100                 105                 110

Val Phe Thr Tyr Ser Glu Phe Asp Gly Ile Leu Gly Leu Ala Tyr Pro
        115                 120                 125

Ser Leu Ala Ser Glu Tyr Ser Val Pro Val Phe Asp Asn Met Met Asp
    130                 135                 140

Arg His Leu Val Ala Arg Asp Leu Phe Ser Val Tyr Met Asp Arg Asn
145                 150                 155                 160

Gly Gln Gly Ser Met Leu Thr Leu Gly Ala Ile Asp Pro Ser Tyr Tyr
                165                 170                 175
```

```
Thr Gly Ser Leu His Trp Val Pro Val Thr Leu Gln Gln Tyr Trp Gln
            180                 185                 190

Phe Thr Val Asp Ser Val Thr Ile Asn Gly Val Ala Val Ala Cys Val
            195                 200                 205

Gly Gly Cys Gln Ala Ile Leu Asp Thr Gly Thr Ser Val Leu Phe Gly
            210                 215                 220

Pro Ser Ser Asp Ile Leu Lys Ile Gln Met Ala Ile Gly Ala Thr Glu
225                 230                 235                 240

Asn Arg Tyr Gly Glu Phe Asp Val Asn Cys Gly Asn Leu Arg Ser Met
            245                 250                 255

Pro Thr Val Val Phe Glu Ile Asn Gly Arg Asp Tyr Pro Leu Ser Pro
            260                 265                 270

Ser Ala Tyr Thr Ser Lys Asp Gln Gly Phe Cys Thr Ser Gly Phe Gln
            275                 280                 285

Gly Asp Asn Asn Ser Glu Leu Trp Ile Leu Gly Asp Val Phe Ile Arg
            290                 295                 300

Glu Tyr Tyr Ser Val Phe Asp Arg Ala Asn Asn Arg Val Gly Leu Ala
305                 310                 315                 320

Lys Ala Ile

<210> SEQ ID NO 6
<211> LENGTH: 323
<212> TYPE: PRT
<213> ORGANISM: Sus scrofa

<400> SEQUENCE: 6

Gly Glu Val Ala Ser Glu Pro Leu Thr Asn Tyr Leu Asp Thr Gln Tyr
1               5                   10                  15

Phe Gly Lys Ile Tyr Ile Gly Thr Pro Pro Gln Glu Phe Thr Val Val
            20                  25                  30

Phe Asp Thr Gly Ser Ser Glu Leu Trp Val Pro Ser Val Tyr Cys Lys
            35                  40                  45

Ser Asp Ala Cys Gln Asn His His Arg Phe Asn Pro Ser Lys Ser Ser
50                  55                  60

Thr Phe Gln Asn Leu Asp Lys Pro Leu Ser Ile Gln Tyr Gly Thr Gly
65                  70                  75                  80

Ser Ile Gln Gly Phe Leu Gly Tyr Asp Thr Val Met Val Ala Gly Ile
            85                  90                  95

Val Asp Ala His Gln Thr Val Gly Leu Ser Thr Gln Glu Pro Ser Asp
            100                 105                 110

Ile Phe Thr Tyr Ser Glu Phe Asp Gly Ile Leu Gly Leu Gly Tyr Pro
            115                 120                 125

Glu Leu Ala Ser Glu Tyr Thr Val Pro Val Phe Asp Asn Met Met His
            130                 135                 140

Arg His Leu Val Ala Gln Asp Leu Phe Ala Val Tyr Met Ser Arg Asn
145                 150                 155                 160

Asp Glu Gly Ser Met Leu Thr Leu Gly Ala Ile Asp Pro Ser Tyr Tyr
            165                 170                 175

Thr Gly Ser Leu His Trp Val Pro Val Thr Met Gln Leu Tyr Trp Gln
            180                 185                 190

Phe Thr Val Asp Ser Val Thr Ile Asn Gly Val Val Val Ala Cys Asn
            195                 200                 205

Gly Gly Cys Gln Ala Ile Leu Asp Thr Gly Thr Ser Met Leu Ala Gly
            210                 215                 220
```

```
Pro Ser Ser Asp Ile Leu Asn Ile Gln Met Ala Ile Gly Ala Thr Glu
225                 230                 235                 240

Ser Gln Tyr Gly Glu Phe Asp Ile Asp Cys Gly Ser Leu Ser Ser Met
            245                 250                 255

Pro Thr Val Val Phe Glu Ile Ser Gly Arg Met Tyr Pro Leu Pro Pro
        260                 265                 270

Ser Ala Tyr Thr Asn Gln Asp Gln Gly Phe Cys Thr Ser Gly Phe Gln
        275                 280                 285

Gly Asp Ser Lys Ser Gln His Trp Ile Leu Gly Val Val Phe Ile Gln
    290                 295                 300

Glu Tyr Tyr Ser Val Phe Asp Arg Ala Asn Asn Arg Val Gly Leu Ala
305                 310                 315                 320

Lys Ala Ile

<210> SEQ ID NO 7
<211> LENGTH: 330
<212> TYPE: PRT
<213> ORGANISM: Bos taurus

<400> SEQUENCE: 7

Ala Ala Thr Leu Val Ser Glu Gln Pro Leu Gln Asn Tyr Leu Asp Thr
1               5                   10                  15

Glu Tyr Phe Gly Thr Ile Gly Ile Gly Thr Pro Ala Gln Asp Phe Thr
            20                  25                  30

Val Ile Phe Asp Thr Gly Ser Ser Asn Leu Trp Val Pro Ser Ile Tyr
        35                  40                  45

Cys Ser Ser Glu Ala Cys Thr Asn His Asn Arg Phe Asn Pro Gln Asp
    50                  55                  60

Ser Ser Thr Tyr Glu Ala Thr Ser Glu Thr Leu Ser Ile Thr Tyr Gly
65                  70                  75                  80

Thr Gly Ser Met Thr Gly Ile Leu Gly Tyr Asp Thr Val Gln Val Gly
                85                  90                  95

Gly Ile Ser Asp Thr Asn Gln Ile Phe Gly Leu Ser Glu Thr Glu Pro
            100                 105                 110

Gly Ser Phe Leu Tyr Tyr Ala Pro Phe Asp Gly Ile Leu Gly Leu Ala
        115                 120                 125

Tyr Pro Ser Ile Ser Ser Ser Gly Ala Thr Pro Val Phe Asp Asn Ile
    130                 135                 140

Trp Asp Gln Gly Leu Val Ser Gln Asp Leu Phe Ser Val Tyr Leu Ser
145                 150                 155                 160

Ser Asn Glu Glu Ser Gly Ser Val Val Ile Phe Gly Asp Ile Asp Ser
                165                 170                 175

Ser Tyr Tyr Ser Gly Ser Leu Asn Trp Val Pro Val Ser Val Glu Gly
            180                 185                 190

Tyr Trp Gln Ile Thr Val Asp Ser Ile Thr Met Asn Gly Glu Ser Ile
        195                 200                 205

Ala Cys Ser Asp Gly Cys Gln Ala Ile Val Asp Thr Gly Thr Ser Leu
    210                 215                 220

Leu Ala Gly Pro Thr Thr Ala Ile Ser Asn Ile Gln Ser Tyr Ile Gly
225                 230                 235                 240

Ala Ser Glu Asp Ser Ser Gly Glu Val Val Ile Ser Cys Ser Ser Ile
                245                 250                 255

Asp Ser Leu Pro Asp Ile Val Phe Thr Ile Asn Gly Val Gln Tyr Pro
            260                 265                 270
```

-continued

```
Val Pro Pro Ser Ala Tyr Ile Leu Gln Ser Asn Gly Ile Cys Ser Ser
            275                 280                 285

Gly Phe Glu Gly Met Asp Ile Ser Thr Ser Ser Gly Asp Leu Trp Ile
290                 295                 300

Leu Gly Asp Val Phe Ile Arg Gln Tyr Phe Thr Val Phe Asp Arg Gly
305                 310                 315                 320

Asn Asn Gln Ile Gly Leu Ala Pro Val Ala
                325                 330

<210> SEQ ID NO 8
<211> LENGTH: 361
<212> TYPE: PRT
<213> ORGANISM: Rhizomucor miehei

<400> SEQUENCE: 8

Ala Ala Ala Asp Gly Ser Val Asp Thr Pro Gly Tyr Tyr Asp Phe Asp
1               5                   10                  15

Leu Glu Glu Tyr Ala Ile Pro Val Ser Ile Gly Thr Pro Gly Gln Asp
                20                  25                  30

Phe Leu Leu Leu Phe Asp Thr Gly Ser Ser Asp Thr Trp Val Pro His
            35                  40                  45

Lys Gly Cys Thr Lys Ser Glu Gly Cys Val Gly Ser Arg Phe Phe Asp
50                  55                  60

Pro Ser Ala Ser Ser Thr Phe Lys Ala Thr Asn Tyr Asn Leu Asn Ile
65                  70                  75                  80

Thr Tyr Gly Thr Gly Gly Ala Asn Gly Leu Tyr Phe Glu Asp Ser Ile
                85                  90                  95

Ala Ile Gly Asp Ile Thr Val Thr Lys Gln Ile Leu Ala Tyr Val Asp
                100                 105                 110

Asn Val Arg Gly Pro Thr Ala Glu Gln Ser Pro Asn Ala Asp Ile Phe
            115                 120                 125

Leu Asp Gly Leu Phe Gly Ala Ala Tyr Pro Asp Asn Thr Ala Met Glu
130                 135                 140

Ala Glu Tyr Gly Ser Thr Tyr Asn Thr Val His Val Asn Leu Tyr Lys
145                 150                 155                 160

Gln Gly Leu Ile Ser Ser Pro Leu Phe Ser Val Tyr Met Asn Thr Asn
                165                 170                 175

Ser Gly Thr Gly Glu Val Val Phe Gly Gly Val Asn Asn Thr Leu Leu
            180                 185                 190

Gly Gly Asp Ile Ala Tyr Thr Asp Val Met Ser Arg Tyr Gly Gly Tyr
        195                 200                 205

Tyr Phe Trp Asp Ala Pro Val Thr Gly Ile Thr Val Asp Gly Ser Ala
210                 215                 220

Ala Val Arg Phe Ser Arg Pro Gln Ala Phe Thr Ile Asp Thr Gly Thr
225                 230                 235                 240

Asn Phe Phe Ile Met Pro Ser Ser Ala Ala Ser Lys Ile Val Lys Ala
                245                 250                 255

Ala Leu Pro Asp Ala Thr Glu Thr Gln Gln Gly Trp Val Val Pro Cys
            260                 265                 270

Ala Ser Tyr Gln Asn Ser Lys Ser Thr Ile Ser Ile Val Met Gln Lys
        275                 280                 285

Ser Gly Ser Ser Ser Asp Thr Ile Glu Ile Ser Val Pro Val Ser Lys
290                 295                 300

Met Leu Leu Pro Val Asp Gln Ser Asn Glu Thr Cys Met Phe Ile Ile
305                 310                 315                 320
```

Leu Pro Asp Gly Gly Asn Gln Tyr Ile Val Gly Asn Leu Phe Leu Arg
            325                 330                 335

Phe Phe Val Asn Val Tyr Asp Phe Gly Asn Asn Arg Ile Gly Phe Ala
            340                 345                 350

Pro Leu Ala Ser Ala Tyr Glu Asn Glu
            355                 360

<210> SEQ ID NO 9
<211> LENGTH: 330
<212> TYPE: PRT
<213> ORGANISM: Endothia sp.

<400> SEQUENCE: 9

Ser Thr Gly Ser Ala Thr Thr Thr Pro Ile Asp Ser Leu Asp Asp Ala
1               5                   10                  15

Tyr Ile Thr Pro Val Gln Ile Gly Thr Pro Ala Gln Thr Leu Asn Leu
            20                  25                  30

Asp Phe Asp Thr Gly Ser Ser Asp Leu Trp Val Phe Ser Ser Glu Thr
        35                  40                  45

Thr Ala Ser Glu Val Asp Gly Gln Thr Ile Tyr Thr Pro Ser Lys Ser
    50                  55                  60

Thr Thr Ala Lys Leu Leu Ser Gly Ala Thr Trp Ser Ile Ser Tyr Gly
65                  70                  75                  80

Asp Gly Ser Ser Ser Gly Asp Val Tyr Thr Asp Thr Val Ser Val
                85                  90                  95

Gly Gly Leu Thr Val Thr Gly Gln Ala Val Glu Ser Ala Lys Lys Val
            100                 105                 110

Ser Ser Ser Phe Thr Glu Asp Ser Thr Ile Asp Gly Leu Leu Gly Leu
            115                 120                 125

Ala Phe Ser Thr Leu Asn Thr Val Ser Pro Thr Gln Gln Lys Thr Phe
    130                 135                 140

Phe Asp Asn Ala Lys Ala Ser Leu Asp Ser Pro Val Phe Thr Ala Asp
145                 150                 155                 160

Leu Gly Tyr His Ala Pro Gly Thr Tyr Asn Phe Gly Phe Ile Asp Thr
                165                 170                 175

Thr Ala Tyr Thr Gly Ser Ile Thr Tyr Thr Ala Val Ser Thr Lys Gln
            180                 185                 190

Gly Phe Trp Glu Trp Thr Ser Thr Gly Tyr Ala Val Gly Ser Gly Thr
        195                 200                 205

Phe Lys Ser Thr Ser Ile Asp Gly Ile Ala Asp Thr Gly Thr Thr Leu
    210                 215                 220

Leu Tyr Leu Pro Ala Thr Val Val Ser Ala Tyr Trp Ala Gln Val Ser
225                 230                 235                 240

Gly Ala Lys Ser Ser Ser Ser Val Gly Gly Tyr Val Phe Pro Cys Ser
                245                 250                 255

Ala Thr Leu Pro Ser Phe Thr Phe Gly Val Gly Ser Ala Arg Ile Val
            260                 265                 270

Ile Pro Gly Asp Tyr Ile Asp Phe Gly Pro Ile Ser Thr Gly Ser Ser
        275                 280                 285

Ser Cys Phe Gly Gly Ile Gln Ser Ser Ala Gly Ile Gly Ile Asn Ile
    290                 295                 300

Phe Gly Asp Val Ala Leu Lys Ala Ala Phe Val Val Phe Asn Gly Ala
305                 310                 315                 320

```
Thr Thr Pro Thr Leu Gly Phe Ala Ser Lys
            325                 330
```

STABILIZATION OF CHYMOSIN BY POLYMERS

CROSS-REFERENCE TO RELATED APPLICATIONS

The present application is a divisional of U.S. patent application Ser. No. 14/902,946, filed Jan. 5, 2016, which is the U.S. National Stage of International Application PCT/EP2014/064913, filed Jul. 11, 2014, which claims priority to European Patent Application No. 13177064.6, filed Jul. 18, 2013.

SEQUENCE LISTING

The instant application contains a Sequence Listing which has been submitted electronically in ASCII format and is hereby incorporated by reference in its entirety. Said ASCII copy, created on Apr. 10, 2018, is named 030427-0217_SL.txt and is 26,154 bytes in size.

FIELD OF THE INVENTION

The present invention relates to liquid or dried granulated milk clotting aspartic protease enzyme composition and a process for isolating milk clotting aspartic protease enzyme of interest.

BACKGROUND ART

Enzymatic coagulation of milk by milk-clotting enzymes, such as chymosin and pepsin, is one of the most important processes in the manufacture of cheeses. Enzymatic milk coagulation is a two-phase process: a first phase where a proteolytic enzyme, chymosin or pepsin, attacks K-casein, resulting in a metastable state of the casein micelle structure and a second phase, where the milk subsequently coagulates and forms a coagulum.

Chymosin (EC 3.4.23.4) and pepsin (EC 3.4.23.1), the milk clotting enzymes of the mammalian stomach, are aspartic proteases belonging to a broad class of peptidases.

Commercial relevant milk-clotting enzyme products are often liquid compositions and in the art is described numerous different ways to try to stabilize the milk-clotting enzyme in the product—e.g. to improve storage stability of the enzyme.

For instance, EP2333056A1 (DSM, date of fling Dec. 4, 2007) describes that formate, acetate, lactate, propionate, malate, fumarate or propanediol may increase stability of aspartic protease enzyme in a liquid composition/product.

WO2012/127005 A1 (DSM) describes a stable liquid chymosin composition comprising inorganic salt in a concentration of 2-100 g/kg and a preservative such as formate, acetate, lactate, propionate, malate, benzoate, sorbate or fumarate, glycol (ethanediol), propylene glycol (propanediol), glycerol, erythritol, xylitol, mannitol, sorbitol, inositol or galactitol.

Polyethylene glycol (PEG) is a polymer of ethylene oxide—it may alternatively be termed polyoxyethylene (POE). PEG is commercially available over a wide range of molecular weights such as from 300 g/mol to 10,000,000 g/mol.

U.S. Pat. No. 5,139,943 (Genencor, published Aug. 18, 1992) describes use of PEG for recovery of microbially produced chymosin via a so-called liquid-liquid two phase system, where PEG and inorganic salt are added to the fermentation media/beer so as to form a liquid-liquid (aqueous) two phase system and then recover/isolate the chymosin from the PEG phase. In the working examples it is described that there were used around 4-5% wt/vol PEG8000 and around 10% wt/vol sodium sulfate salt in order to be able to obtain the liquid-liquid (aqueous) two phase system.

U.S. Pat. No. 7,998,705B2 (Fujifilm, published Aug. 16, 2011) describes use of PEG to increase the dynamic binding capacity of high salt solution (e.g. cell culture broth) on a ion exchange chromatography resin and thereby be able to purify a protein of interest. As examples of proteins of interest are mentioned bovine globulin, bovine serum albumin and lysozyme—a milk-clotting enzyme (such as e.g. chymosin) is not explicitly mentioned. In working examples (see e.g. Example 1) is described that best protein recovery were obtained by using around 6% w/v of PEG (preferably PEG4600)—for instance using only 0.5% PEG gave virtually no positive effect on protein recovery/isolation.

As known in the art—the term PEGylation relates to the act of covalently coupling a polyethylene glycol (PEG) structure to another larger molecule, for example, a therapeutic protein (which is then referred to as PEGylated). PEGylation, by increasing the molecular weight of a molecule, may impart several significant pharmacological advantages over the unmodified form, such as: improved drug solubility, reduced dosage frequency.

US2011/0008846A1 (Qiagen) describes PEGylation of industrially used enzymes and Rennin (Chymosin) is mentioned as an example of a suitable industrially used enzyme within a long list of mentioned suitable industrially used enzymes. The working example only relates to PEGylation of a Polymerase—i.e. there is no working example relating to PEGylation of Rennin (Chymosin).

It may here be relevant to note that none of above cited prior art references describe that PEG may increase the stability of aspartic protease milk-clotting enzymes such as e.g. chymosins.

DE1492060A1 (Nordmark-Werke GmbH, published in 1969) discloses a method for making a pepsin composition by adding PEG with a molecular weight of 400-6000 at a concentration of 1-20 wt % (corresponds to 10000 to 200000 ppm).

SUMMARY OF THE INVENTION

A problem to be solved by the present invention is to provide a new milk clotting aspartic protease enzyme (e.g. chymosin) composition, wherein the aspartic protease has increased stability and/or activity.

Another problem to be solved by the present invention is to provide a novel method for isolating an aspartic protease (e.g. chymosin), wherein the method may give increased activity of the isolated aspartic protease composition.

The solution is based on that the present inventors have identified that by adding PEG or a similar substituted polyoxyethylene (e.g. Brij35) to chymosin one significantly improves the physical stability of the chymosin.

The structures of PEG and Brij35 are shown in FIG. 1 herein.

As discussed in working Examples herein—recombinantly produced bovine chymosin (CHY-MAX®, Chr. Hansen A/S) and camel chymosin (CHY-MAX® M, Chr. Hansen A/S) were purified by chromatography, where PEG8000 and Brij35 were added before elution from the column or PEG8000 and Brij35 were added to the elution buffer.

Samples containing PEG8000 or Brij35 had 1.5 to two-fold increased specific activity over control sample purified without addition of PEG/Brij35 (see discussion in working Example 2 herein and FIG. 2A and FIG. 2B herein).

The effect of the significant increased specific activity of the chymosin enzymes was surprising to the present inventors, among other reasons, because it could be seen immediately after isolation of protein.

This immediate observed increased specific activity cannot be explained by that PEG/Brij35 only e.g. increase longer term storage stability of the enzymes by decreasing possible longer term storage precipitation problems, since there is no significant precipitation of the enzymes immediately after isolation of protein according to the purification protocol/method used in the working Examples herein—i.e. also in the control experiment without addition of addition of PEG/Brij35 there is no significant precipitation of the enzymes immediately after isolation of protein.

Without being limited to theory—it is believed that PEG/Brij35 provide increased conformational stability to the chymosins and this could explain the immediately observed increased specific activity observed in working Examples herein.

Without being limited to theory—it is believed that in the prior art it has not been described or suggested that PEG or structurally similar polymers may increase the stability of aspartic protease milk-clotting enzymes such as e.g. chymosins—in particular it has not been described that conformational stability may be increased.

Conformational stability of an enzyme is illustrated in FIG. 3 herein.

As known in the art—loss of conformation equals loss of activity of the enzyme.

In working Examples herein—it was also demonstrated that addition of PEG increased the longer term storage stability of a liquid and/or granulated chymosin composition.

Without being limited to theory—it may be that for aspartic protease milk-clotting enzymes (such as e.g. chymosins) loss of structural conformation could result in increased precipitation of the enzymes during e.g. longer term storage in e.g. a liquid formulation.

Accordingly—it may be that PEG helps to decrease precipitation of the milk-clotting enzymes during the storage e.g. due to that it provides conformational stability to the enzymes.

Polyethylene glycol (PEG) is a polymer of ethylene oxide and may alternatively be termed polyoxyethylene (POE)—a structure-based IUPAC name for PEG is poly(oxyethylene).

As understood by the skilled person in the present context—Brij35 may be termed a substituted polyoxyethylene, where the substituent may be seen as the "C12" structure as shown in FIG. 1 herein.

As understood by the skilled person in the present context—polymers such as e.g. Polyvinylpolypyrrolidone, Polyvinyl alcohol, Polyvinyl acetate, Polyacrylonitrile, Polyacrylate or Polymethacrylate may be considered structurally and functionally related to PEG/Brij35.

As known in the art—polymers may be a heteropolymer or copolymer, which is a polymer derived from two (or more) monomeric species, as opposed to a homopolymer where only one monomer is used.

As understood by the skilled person in the present context—a copolymer which is derived from following two (or more) of monomeric species ethylene oxide, vinylpolypyrrolidone, vinyl alcohol, vinyl acetate, acrylonitrile, acrylate or methacrylate may in the present context be considered structurally and functionally related.

Without being limited to theory—it is believed that there is no significant technical reason to believe that such polymers structurally and functionally related to PEG/Brij35 would not give herein relevant improvements of milk-clotting aspartic protease stability.

In relevant working Examples herein were used PEG8000 and Brij35, which respectively have a mean molecular mass of 8000 g/mol and 1225 g/mol.

In the present context it is believed that a herein relevant polymer with a molecular mass (alternatively termed molecular weight (MW)) from 200 g/mol to 50.000 g/mol would be suitable.

In the present context it is believed that a herein relevant polymer with a repeating monomer/element number (so-called "n" number) from n=5 to n=1250 would be suitable.

As an example can be seen in FIG. 1 that Brij35 has n=23.

As known in the art—PEG with n=1250 has a MW of around 50.000 g/mol and PEG8000 has a MW of around 8.000 g/mol and n=200.

Figure 6:
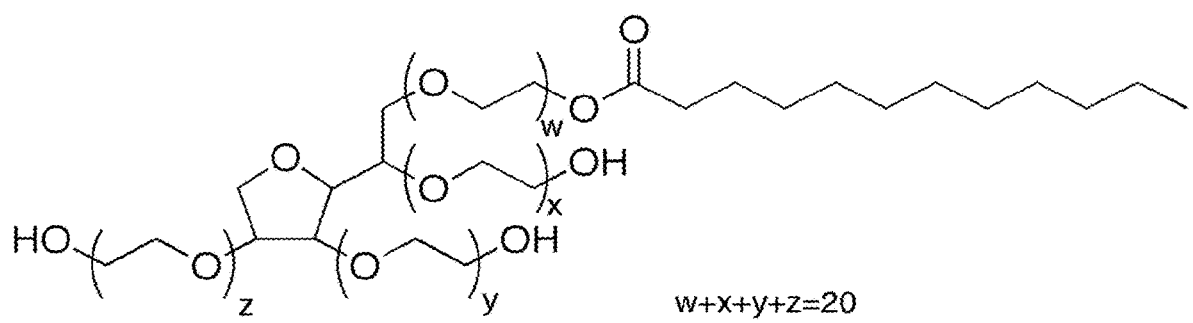

In FIG. 6 is shown an example of another herein relevant polymer polysorbate 20, which comprises a sum of 20 ethylene oxide monomers.

In working Example 4 herein is demonstrated that addition of polysorbate 20 increased the stability the tested liquid milk clotting aspartic protease enzyme compositions.

As understood by the skilled person in the present context—polysorbate 20 is a polymer with a repeating monomer/element number (so-called "n" number) of 20 in relation to characteristic (c) of the first aspect herein.

For instance, using the nomenclature of FIG. 6—polysorbate 20 may e.g. have w, x, y and z=5—i.e. 4 groups of monomers each having n=5.

Accordingly, as the skilled person would understand in the present context—such a polysorbate 20 polymer will in the present context be a polymer with n=5×4=20 in relation to characteristic (c) of the first aspect herein.

As understood by the skilled person in the present context—what is relevant in the present context is the number of herein relevant monomers (e.g. ethylene oxide) present in the polymer as such.

For instance, the total number of herein relevant monomers (e.g. ethylene oxide) present in the polymer as such is important for e.g. the herein relevant molecular mass of the polymer.

Accordingly, as understood by the skilled person in the present context—the term "repeating monomer" in in relation to characteristic (c) of the first aspect herein relates to the total number of herein relevant monomers (e.g. ethylene oxide) present in the polymer as such.

As known in the art—milk clotting aspartic protease enzymes may be seen as structurally relatively similar.

As known in the art—different natural wildtype milk clotting aspartic protease polypeptide sequences obtained from different mammalian or fungal species (such as e.g. bovines, camels, sheep, pigs, or mucor) are having a relatively high tertiary structural similarity.

In FIG. 4 herein there is provided an alignment of herein relevant different milk clotting chymosin sequences from different mammalian species (cow, buffalo, goat, sheep, camel and pig)—as can be seen in FIG. 4 they have a close sequence relationship and are known to have a very high tertiary structural similarity.

In FIG. 5 herein there is provided an alignment of herein relevant commercially available different milk clotting aspartic protease enzymes sequences from different mammalian or fungal species (camel chymosin, cow chymosin, cow pepsin, fungal mucor pepsin and fungal Endothia pepsin).

It may be said that the 5 different sequences of FIG. 5 are not highly identical—but as known to the skilled person all these 5 different milk clotting aspartic protease enzymes are known to have a high tertiary structural similarity.

As discussed above and shown in working Examples herein—the herein relevant improved/increased stability have been demonstrated for bovine chymosin and camel chymosin.

Without being limited to theory—it is believed that there is no significant technical reason to believe that the herein relevant improved/increased stability effect should not be relevant for milk clotting aspartic protease enzymes in general—as discussed above, they are known to have a high tertiary structural similarity and as understood by the skilled person in the present context this tertiary structural similarity makes it plausible that the herein described polymer-enzyme interaction to get improved stability would be a general class effect of the structural similar herein relevant milk clotting aspartic protease enzymes.

Accordingly, a first aspect of the invention relates to a liquid milk clotting aspartic protease enzyme composition comprising:
  (i): milk clotting aspartic protease enzyme at a strength of from 25 IMCU/g of the composition to 30000 IMCU/g of the composition;
  (ii): polymer in a concentration from 1 ppm to 10000 ppm (w/w), and
  (iii) a salt in a concentration from 1 to 350 g/kg;
and wherein the pH of the composition is from 2 to 8;
and wherein the polymer is a polymer having following characteristics (a), (b) and (c):
  (a): the polymer is a polymer of at least one monomer selected from the group of monomers consisting of: ethylene oxide, vinylpolypyrrolidone, vinyl alcohol, vinyl acetate, acrylonitrile, acrylate and methacrylate; and
  (b): the polymer is a polymer with a molecular mass from 200 g/mol to 50.000 g/mol; and
  (c): the polymer is a polymer with a repeating monomer/element number (so-called "n" number) from n=5 to n=1250; and
  (D): optionally the polymer having the characteristics (a), (b) and (c) above may be a substituted polymer comprising one or more substituent compound(s) different from the monomers of characteristic (a) and if the polymer is a substituted polymer the molecular mass of the substituted polymer as such is within the range of characteristic (b) and the molecular mass of the substituent compound(s) is less than the molecular mass of the polymer part of the substituted polymer.

As understood by the skilled person in the present context—the term "IMCU/g of the composition" in item (i) of the first and/or aspect relates to IMCU enzyme activity per gram of the composition as such.

The same goes for the term "g/kg" in relation to item (iii) of the first aspect—i.e. it relates to gram salt per kg of the composition as such.

It may be preferred that the liquid composition of the first aspect has a total weight of from 10 g to 10000 kg.

As known to the skilled person in the present context—a herein relevant liquid composition of the first aspect that has a weight of 1 kg will approximately have a volume of 1 liter.

As discussed above—Brij35 may be termed a substituted polyoxyethylene, where the substituent may be seen as the "C12" structure as shown in FIG. 1 herein and Brij35, has a mean molecular mass of around 1225 g/mol.

Accordingly, Brij35 may be seen as an example of a substituted polymer of optional characteristic (D) of the first aspect, wherein the substituent compound is the "C12" structure as shown in FIG. 1 herein and molecular mass of the substituted polymer as such is 1225 g/mol and the molecular mass of the substituent compound ("C12" structure) is significantly less than the molecular mass of the polymer part (polymer of ethylene oxide with n=23).

As understood by the skilled person in the present context—it is the polymer part having characteristics (a), (b) and (c) which are considered of most importance and possible substituent compound(s) of optionally characteristic (D) may be seen as of less importance.

As discussed above—in FIG. 6 is shown an example of another herein relevant polymer polysorbate 20, which comprises a sum of 20 ethylene oxide monomers.

Like Brij35 is polysorbate 20 (alternatively termed Tween20) understood to be a substituted polymer in the present context. In polysorbate 20 are the substituent compounds/groups the sorbitan and laurate groups and the molecular mass of the substituent compounds/groups are significantly less than the molecular mass of the polymer part (i.e. the 20 ethylene oxide monomers).

As understood by the skilled person in the present context—the generic term "polymer" covers the more specific term "substituted polymer" in the sense that a polymer may be substituted or un-substituted.

As discussed above—in U.S. Pat. No. 5,139,943 was used around 4-5% w/vol PEG8000 in order to be able to obtain the liquid-liquid (aqueous) two phase system and in U.S. Pat. No. 7,998,705B2 was used around 6% w/v of PEG in order to get a significant increased dynamic binding capacity on an ion exchange chromatography resin.

In the composition of the first aspect is only used from 1 ppm to 10000 ppm w/w (i.e. from 0.0001% to 1.0% w/w) of the herein described polymer (e.g. PEG)—i.e. an amount which is significantly less than required in above discussed prior art references.

Accordingly and without being limited to theory—one may say that one needs to use significantly less amounts of the herein relevant polymers (e.g. PEG) in order to obtain the herein described increased conformational stability effect to the milk clotting enzyme as compared to the amounts used in above described prior art.

Herein relevant polymers (e.g. PEG) may be described as processing aids.

The first aspect herein relates to a liquid composition—however, milk clotting aspartic protease enzymes (e.g. chymosin) may also be commercialized as dried granulated composition/product.

Accordingly, a second aspect of the invention relates to a dried granulated milk clotting aspartic protease enzyme composition comprising:
  (i): milk clotting aspartic protease enzyme at a strength of from 25 IMCU/g of the composition to 30000 IMCU/g of the composition;
  (ii): polymer in a concentration from 1 ppm to 10000 ppm (w/w), and
  (iii) a salt;
and wherein the pH of the composition suspended in water is from 2 to 8;
and wherein the polymer is a polymer having the characteristics (a), (b) and (c) and optionally (D) of first aspect.

As discussed above—PEGylation relates to the act of covalently coupling a polyethylene glycol (PEG) structure to another larger molecule, for example, a therapeutic protein (which is then referred to as PEGylated).

As understood by the skilled person in the present context—the essence of the present invention does not as such relate to PEGylation.

Accordingly and as understood by the skilled person in the present context—liquid and/or dried milk clotting aspartic protease enzyme composition as described herein is preferably not a composition, wherein the polymer is covalently coupled to the milk clotting aspartic protease enzyme.

As discussed herein—an advantage of milk clotting aspartic protease enzyme composition as described herein is that it is more storage stable.

Accordingly, a third aspect of the invention relates to a method for storage of a milk clotting aspartic protease enzyme, wherein the method comprises following steps:
(a): providing a milk clotting aspartic protease enzyme composition of first or second aspect or any herein relevant embodiments thereof; and
(b): storage of the composition at a period from 90 days to 2000 days at a temperature from −10° C. to 50° C.

A milk clotting aspartic protease enzyme composition as described herein may be used according to the art—e.g. to make a food or feed product of interest (such as e.g. a milk based product of interest that e.g. could be a cheese product).

Accordingly, a fourth aspect of the invention relates to a method for making a food or feed product comprising adding an effective amount of a milk clotting aspartic protease enzyme composition of any of first or second aspect or any herein relevant embodiments thereof to the food or feed ingredient(s) and carrying out further manufacturing steps to obtain the food or feed product.

As discussed above—by use of a herein relevant polymer as described herein it is possible to isolate/purify milk clotting aspartic protease enzyme sample with increased specific activity.

Accordingly, a fifth aspect of the invention relates to a process for isolating a milk clotting aspartic protease enzyme of interest from an aqueous medium comprising such an enzyme of interest, wherein the method comprises the steps of:
  (i): obtaining an aqueous sample consisting of a number of components including the aspartic protease;
  (ii): adding polymer in a concentration from 1 ppm to 10000 ppm to the aqueous sample of step (i) to get a polymer containing sample; and
  (iii): isolating the aspartic protease from the polymer containing sample of step (ii) and thereby obtaining the isolated milk clotting aspartic protease enzyme of interest;
wherein the polymer is a polymer having the characteristics (a), (b) and (c) and optionally (D) of first aspect.

As discussed above—in U.S. Pat. No. 5,139,943 was used around 4-5% w/vol PEG8000 in order to be able to obtain the liquid-liquid (aqueous) two phase system and in U.S. Pat. No. 7,998,705B2 was used around 6% w/v of PEG in order to get a significant increased dynamic binding capacity on an ion exchange chromatography resin.

In the process of the fifth aspect is only used from 1 ppm to 10000 ppm w/w (i.e. from 0.0001% to 1.0%) of the herein described polymer (e.g. PEG)—i.e. an amount which is significant less than required in above discussed prior art references.

Definitions

All definitions of herein relevant terms are in accordance of what would be understood by the skilled person in relation to the herein relevant technical context.

The term "milk-clotting enzyme" refers to an enzyme with milk-clotting enzymatic activity—i.e. an active milk-clotting enzyme. The milk-clotting activity (C) may be expressed in International Milk-Clotting Units (IMCU) per ml or IMCU per g. The skilled person knows how to determine herein relevant milk-clotting enzymatic activity. In working Example 1 herein is provided an example of a standard method to determine milk-clotting enzymatic activity and specific milk-clotting enzymatic activity. As known in the art—specific clotting activity (IMCU/mg total protein) is determined by dividing the clotting activity (IMCU/ml) by the total protein content (mg total protein per ml).

The term "ppm" refers to parts-per-million. As known in the art—the unit "ppm" can be used for a mass fraction and the term ppm is herein used in relation to mass fraction (w/w). For instance, a herein relevant polymer in e.g. a concentration of 500 ppm (w/w) in relation to e.g. a herein relevant milk clotting aspartic protease enzyme composition relates to that the polymer is present at 500 times 1-millionth of a gram per gram of sample composition, which corresponds to 0.05% w/w. Said in other words—1 ppm (w/w) corresponds to 0.0001% (w/w) and 10000 ppm (w/w) corresponds to 1% (w/w).

The term "Sequence Identity" relates to the relatedness between two amino acid sequences.

For purposes of the present invention, the degree of sequence identity between two amino acid sequences is determined according to the art and preferably determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment− Total Number of Gaps in Alignment).

The term "variant" means a peptide having milk-clotting enzymatic activity comprising an alteration, i.e., a substitution, insertion, and/or deletion, at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The amino acid may be natural or unnatural amino acids—for instance, substitution with e.g. a particularly D-isomers (or D-forms) of e.g. D-alanine could theoretically be possible.

Embodiment of the present invention is described below, by way of examples only.

DRAWINGS

FIG. 1: Structures of PEG and Brij35

FIG. 2A and FIG. 2B: Show the results of addition of 0.1% PEG8000 or Brij35 to the elution buffer as compared to control experiments without addition of PEG8000 or Brij35. See e.g. working Example 2 herein for further details. In FIG. 2A is shown data for camel chymosin and in FIG. 2B is shown data for bovine chymosin.

FIG. 3: Conformational stability of an enzyme is illustrated.

FIG. 4: An alignment of herein relevant different milk clotting chymosin sequences from different mammalian species (cow (SEQ ID NO: 1), buffalo (SEQ ID NO: 2), goat (SEQ ID NO: D, sheep (SEQ ID NO: 4), camel (SEQ ID NO: 5) and pig (SEQ ID NO: 6)). All the sequences of FIG. 4 are publicly available.

FIG. 5: An alignment of herein relevant commercially available different milk clotting aspartic protease enzymes sequences from different mammalian or fungal species (camel chymosin (SEQ ID NO: 5), cow chymosin (SEQ ID NO: 1), cow pepsin (SEQ ID NO: 7), fungal mucor pepsin (SEQ ID NO: 8) and fungal Endothia pepsin (SEQ ID NO: 9)). All the sequences of FIG. 5 are publicly available.

FIG. 6: Structure of another herein relevant polymer polysorbate 20, which comprises a sum of 20 ethylene oxide monomers.

DETAILED DESCRIPTION OF THE INVENTION

Milk Clotting Aspartic Protease Enzyme

The discussion of specific embodiments/examples of herein relevant milk clotting aspartic protease enzymes below is relevant for all the aspects of the invention as discussed herein.

In a preferred embodiment, the milk clotting aspartic protease enzyme is a milk-clotting enzyme selected from the group consisting of chymosin (EC 3.4.23.4), pepsin (EC 3.4.23.1) and mucorpepsin (EC 3.4.23.23).

A preferred milk clotting aspartic protease enzyme is *Camelius dromedarius* chymosin as described in e.g. WO02/36752A2 (Chr. Hansen). It may herein alternatively be termed camel chymosin and the publically known mature polypeptide amino acid sequence is shown in FIG. 5 herein.

As known in the art—it is routine work for the skilled person to make variants (i.e. amino acid modifications) of an enzyme of interest without significantly changing the characteristics of the enzyme.

Accordingly, in a preferred embodiment the milk clotting aspartic protease enzyme is *Camelius dromedarius* chymosin comprising the polypeptide amino acid sequence shown in FIG. 5 herein (termed "Camel_chymosin") or a variant of *Camelius dromedarius* chymosin, wherein the variant comprises a polypeptide sequence which has at least 90% (preferably at least 95%, more preferably at least 99%) sequence identity with the camel chymosin polypeptide amino acid sequence shown in FIG. 5 herein.

A preferred milk clotting aspartic protease enzyme is bovine chymosin. It may herein alternatively be termed cow chymosin and the publically known mature polypeptide amino acid sequence is shown in FIG. 5 herein.

Accordingly, in a preferred embodiment the milk clotting aspartic protease enzyme is bovine chymosin comprising the polypeptide amino acid sequence shown in FIG. 5 herein (termed "Cow_chymosin") or a variant of bovine chymosin, wherein the variant comprises a polypeptide sequence which has at least 90% (preferably at least 95%, more preferably at least 99%) sequence identity with the bovine chymosin polypeptide amino acid sequence shown in FIG. 5 herein.

A preferred milk clotting aspartic protease enzyme is bovine pepsin. It may herein alternatively be termed cow pepsin and the publically known mature polypeptide amino acid sequence is shown in FIG. 5 herein.

Accordingly, in a preferred embodiment the milk clotting aspartic protease enzyme is bovine pepsin comprising the polypeptide amino acid sequence shown in FIG. 5 herein (termed "Cow_pepsin") or a variant of bovine pepsin, wherein the variant comprises a polypeptide sequence which has at least 90% (preferably at least 95%, more preferably at least 99%) sequence identity with the bovine pepsin polypeptide amino acid sequence shown in FIG. 5 herein.

A preferred milk clotting aspartic protease enzyme is Mucor pepsin (see e.g. EP0805866B1 (Harboe et al, Chr. Hansen A/S, Denmark)). The publically known mature polypeptide amino acid sequence is shown in FIG. 5 herein.

Accordingly, in a preferred embodiment the milk clotting aspartic protease enzyme is Mucor pepsin comprising the polypeptide amino acid sequence shown in FIG. 5 herein (termed "Mucor") or a variant of Mucor pepsin, wherein the variant comprises a polypeptide sequence which has at least 90% (preferably at least 95%, more preferably at least 99%) sequence identity with the Mucor pepsin polypeptide amino acid sequence shown in FIG. 5 herein.

A preferred milk clotting aspartic protease enzyme is Endothia pepsin. The publically known mature polypeptide amino acid sequence is shown in FIG. 5 herein.

Accordingly, in a preferred embodiment the milk clotting aspartic protease enzyme is Mucor pepsin comprising the polypeptide amino acid sequence shown in FIG. 5 herein (termed "Endothia") or a variant of Endothia pepsin, wherein the variant comprises a polypeptide sequence which has at least 90% (preferably at least 95%, more preferably at least 99%) sequence identity with the Endothia pepsin polypeptide amino acid sequence shown in FIG. 5 herein.

Polymer

As discussed above—the polymer of the liquid milk clotting aspartic protease enzyme composition of the first aspect, the dried milk clotting aspartic protease enzyme composition of the second aspect and/or the process for isolating a milk clotting aspartic protease enzyme of interest of the fifth aspect is a polymer having following characteristics (a), (b) and (c) or optionally (D):

(a): the polymer is a polymer of at least one monomer selected from the group of monomers consisting of: ethylene oxide, vinylpolypyrrolidone, vinyl alcohol, vinyl acetate, acrylonitrile, acrylate and methacrylate; and (b): the polymer is a polymer with a molecular mass from 200 g/mol to 50.000 g/mol; and (c): the polymer is a polymer with a repeating monomer/element number (so-called "n" number) from n=5 to n=1250; and (D): optionally the polymer having the characteristics (a), (b) and (c) above may be a substituted polymer comprising one or more substituent compound(s) different from the monomers of characteristic (a) and if the polymer is a substituted polymer the molecular mass of the substituted polymer as such is within the range of characteristic (b) and the molecular mass of the substituent compound(s) is less than the molecular mass of the polymer part of the substituted polymer.

The discussion of specific embodiments/examples of herein relevant polymers below is relevant for all the aspects of the invention as discussed herein.

As understood by the skilled person in the present context—a polymer of at least two or more monomers of characteristic (a) is what in the art may be termed a heteropolymer or copolymer which is a polymer derived from two (or more) monomeric species, as opposed to a homopolymer where only one monomer is used—i.e. a polymer of only monomer of characteristic (a) is what in the art may be termed a homopolymer.

In relation to characteristic (a) is may be preferred that the polymer is a polymer of two different monomers selected from the group of characteristic (a).

Preferably, the polymer is a homopolymer.

In relation to the optional characteristic (D)—it is preferred that the molecular mass of the substituent compound(s) is at least 2 times less than the molecular mass of the polymer part of the substituted polymer, more preferably that the molecular mass of the substituent compound(s) is at least 4 times less than the molecular mass of the polymer part of the substituted polymer.

A herein preferred substituted polymer is Brij35, which has the structure as shown in FIG. 1 herein.

The substituent compound may e.g. be a $C_1$-$C_{25}$ alkyl (e.g. $C_1$-$C_{25}$ substituted alkyl), $C_1$-$C_{25}$ alkenyl (e.g. $C_1$-$C_{25}$ substituted alkenyl)—wherein the alkyl and/or alkenyl may e.g. be linear, cyclic or branched.

As known in the art—polymers may e.g. also comprise e.g. Cl, Br and similar substituent compounds—i.e. e.g. Cl, Br may also be example of substituent compounds herein.

Preferably, the polymer is a polymer with a molecular mass from 750 g/mol to 30.000 g/mol, such as e.g. a polymer with a molecular mass from 2000 g/mol to 20.000 g/mol or such as e.g. a polymer with a molecular mass from 5000 g/mol to 15.000 g/mol.

As understood by the skilled person in the present context—a preferred molecular mass may depend on the specific type of polymer or whether it is a substituted polymer (e.g. like Brij35) or not.

Preferably, the polymer is a polymer with a repeating monomer/element number (so-called "n" number) from n=20 to n=500, such as e.g. a polymer a polymer with a repeating monomer/element number (so-called "n" number) from n=100 to n=300.

Like for the molecular mass and as understood by the skilled person in the present context—a preferred "n" number may depend on the specific type of polymer or whether it is a substituted polymer (e.g. like Brij35) or not.

In the present context—it may be considered as routine work for the skilled person to identify an optimal molecular mass and/or "n" number for a particular herein relevant polymer of interest in order to obtain the herein described stability improvement in relation to e.g. a particular milk clotting aspartic protease enzyme of interest (such as e.g. bovine or camel chymosin).

Preferably, the polymer is Polyethylene glycol (PEG) Polyvinylpolypyrrolidone, Polyvinyl alcohol, Polyvinyl acetate, Polyacrylonitrile, Polyacrylate, Polymethacrylate, polysorbate or Brij35.

When the polymer is Polyethylene glycol (PEG) Polyvinylpolypyrrolidone, Polyvinyl alcohol, Polyvinyl acetate, Polyacrylonitrile, Polyacrylate or Polymethacrylate—it is preferred that the polymer is a polymer with a molecular mass from 1500 g/mol to 40000 g/mol, such as e.g. a polymer with a molecular mass from 2000 g/mol to 30000 g/mol or such as e.g. a polymer with a molecular mass from 5000 g/mol to 15000 g/mol.

Preferably the polymer is Polyethylene glycol (PEG), polysorbate 20 or Brij35.

In relation to PEG it may be preferred that the polymer is a polymer with a molecular mass from 1500 g/mol to 40000 g/mol, such as e.g. a polymer with a molecular mass from 2000 g/mol to 30000 g/mol or more preferred polymer with a molecular mass from 5000 g/mol to 15000 g/mol.

First and/or Second Aspect—a Liquid and/or Dried Milk Clotting Aspartic Protease Enzyme Composition As discussed above—the first aspect of the invention relates to a liquid milk clotting aspartic protease enzyme composition comprising:
(i): milk clotting aspartic protease enzyme at a strength of from 25 IMCU/g of the composition to 30000 IMCU/g of the composition;
(ii): polymer in a concentration from 1 ppm to 10000 ppm (w/w), and
(iii) a salt in a concentration from 1 to 350 g/kg;
and wherein the pH of the composition is from 2 to 8;
and wherein the polymer is a polymer having following characteristics (a), (b) and (c) and optionally (D): [as described herein].

As discussed above—the second aspect of the invention relates to a dried granulated milk clotting aspartic protease enzyme composition comprising:
(i): milk clotting aspartic protease enzyme at a strength of from 25 IMCU/g of the composition to 30000 IMCU/g of the composition;
(ii): polymer in a concentration from 1 ppm to 10000 ppm (w/w), and
(iii) a salt;
and wherein the pH of the composition suspended in water is from 2 to 8;
and wherein the polymer is a polymer having the characteristics (a), (b) and (c) and optionally (D): [as described herein].

For both the liquid and the dried composition—preferred examples/embodiments of milk clotting aspartic protease enzymes are described above.

For both the liquid and the dried composition—preferred examples/embodiments of polymer are described above.

For both the liquid and the dried composition—it is preferred that the enzyme strength in item (i) is a strength of from 100 IMCU/g of the composition to 10000 IMCU/g of the composition, more preferably a strength of from 500 IMCU/g of the composition to 6000 IMCU/g of the composition.

For both the liquid and the dried composition—it is preferred that the polymer concentration in item (ii) is in a concentration from 1 ppm to 5000 ppm (w/w).

For both the liquid and the dried composition—it is preferred that the polymer concentration in item (ii) is in a concentration from 1 ppm to 3000 ppm (w/w).

For both the liquid and the dried composition—it is preferred that the polymer concentration in item (ii) is in a concentration from 10 ppm to 5000 ppm (w/w), more preferably is in a concentration from 50 ppm to 4000 ppm (w/w) and even more preferably is in a concentration from 100 ppm to 3000 ppm (w/w).

It may be relevant that the polymer concentration in item (ii) is in a concentration from 160 ppm to 5000 ppm (w/w), such as e.g. from 175 ppm to 4000 ppm (w/w).

It may be relevant that the polymer concentration in item (ii) is in a concentration from 5 ppm to 145 ppm (w/w), such as e.g. from 10 ppm to 130 ppm (w/w).

For the liquid composition—the salt in item (iii) is preferably in a concentration from 10 to 300 g/kg, more preferably is in a concentration from 25 to 250 g/kg.

As known to the skilled person—for the dried composition the salt concentration in item (iii) may be relatively high—such as e.g. from 50% (w/w) to 99.9% (w/w) or such as e.g. from 80% (w/w) to 99% (w/w).

For both the liquid and the dried composition—it is preferred that the salt is an inorganic salt—preferably wherein the inorganic salt is selected from the group of NaCl, KCl, Na$_2$SO$_4$, (NH$_4$)$_2$SO$_4$, K$_2$HPO$_4$, KH$_2$PO$_4$, Na$_2$HPO$_4$ or NaH$_2$PO$_4$ or a combination thereof. Most preferably, the salt is NaCl.

Both the liquid and the dried composition may comprise further additives/compounds such as e.g. a preservative.

As known to the skilled person—preservative may generally be added in a concentration sufficient to prevent microbial growth during shelf life of the product.

Examples of preservatives may be e.g. weak organic acids such as formate, acetate, lactate, propionate, malate, benzoate, sorbate or fumarate. Parabens (alkyl esters of parahydroxybenzoate) may also be used as preservative. Glycerol or propanediol has also been described as preservatives.

Both the liquid and the dried composition—it is preferred that the pH is from 3 to 7, more preferably that the pH is from 4 to 6.5 and even more preferably that the pH is from 5 to 6.

Preferably, the liquid composition is an aqueous composition, for instance an aqueous solution. As used herein an aqueous composition or aqueous solution encompasses any composition or solution comprising water, for instance at least 20 wt % of water, for instance at least 40 wt % of water. Preferably, a composition according to the invention comprises at least 50, 60, 70 or 80 wt % of water. More preferably, the composition of the invention comprises at least 85, 90 or 95 wt % of water.

As discussed in working Example 2 herein and as can be seen in FIG. 2A and FIG. 2B herein—by using of a polymer as described herein it was possible to obtain milk clotting aspartic protease enzyme compositions with significantly increased specific activity of the enzyme.

As can be seen in FIG. 2A herein—by using of a polymer as described herein it was possible to obtain camel enzyme compositions, wherein the specific activity of the enzymes were higher than 350 IMCU/mg total protein and in the comparative experiment (i.e. without addition of polymer) was the specific activity of the enzyme only around 200 IMCU/mg total protein.

As can be seen in FIG. 2B herein—by using of a polymer as described herein it was possible to obtain bovine enzyme compositions, wherein the specific activity of the enzymes were higher than 150 IMCU/mg total protein and in the comparative experiment (i.e. without addition of polymer) was the specific activity of the enzyme only around 125 IMCU/mg total protein.

Accordingly, in a preferred embodiment for both the liquid and the dried composition:
  is the specific activity of the milk clotting aspartic protease enzyme higher than 300 IMCU/mg total milk clotting aspartic protease enzyme protein, more preferably is the specific activity milk clotting aspartic protease enzyme higher than 350 IMCU/mg total milk clotting aspartic protease enzyme protein, wherein the milk clotting aspartic protease enzyme is *Camelius dromedarius* chymosin comprising the polypeptide amino acid sequence shown in FIG. 5 herein (termed "Camel_chymosin") or a variant of *Camelius dromedarius* chymosin, wherein the variant comprises a polypeptide sequence which has at least 90% (preferably at least 95%, more preferably at least 99%) sequence identity with the camel chymosin polypeptide amino acid sequence shown in FIG. 5 herein; or
  is the specific activity of the milk clotting aspartic protease enzyme higher than 150 IMCU/mg total milk clotting aspartic protease enzyme protein, more preferably is the specific activity milk clotting aspartic protease enzyme higher than 165 IMCU/mg total milk clotting aspartic protease enzyme protein, wherein the milk clotting aspartic protease enzyme is bovine chymosin comprising the polypeptide amino acid sequence shown in FIG. 5 herein (termed "Cow_chymosin") or a variant of bovine chymosin, wherein the variant comprises a polypeptide sequence which has at least 90% (preferably at least 95%, more preferably at least 99%) sequence identity with the bovine chymosin polypeptide amino acid sequence shown in FIG. 5 herein.

It may be preferred that the liquid composition as described herein has a total weight of from 10 g to 10000 kg, such as e.g. from 100 g to 3000 kg.

It may be preferred that the dried granulated composition as described herein has a total weight of from 0.25 g to 200 kg, such as e.g. from 0.5 g to 50 kg.

It is preferred that the composition is a liquid milk clotting aspartic protease enzyme composition as described herein.

Third Aspect—a Method for Storage

As discussed above—the third aspect of the invention relates to a method for storage of a milk clotting aspartic protease enzyme, wherein the method comprises following steps:

(a): providing a milk clotting aspartic protease enzyme composition of first or second aspect or any herein relevant embodiments thereof; and (b): storage of the composition at a period from 90 days to 2000 days at a temperature from −10° C. to 50° C.

Preferably, the storage temperature in step (b) is a temperature from 4° C. to 38° C.

It may be preferred that the storage period in step (b) is a period from 180 days to 500 days.

Fourth Aspect—a Method for a Method for Making a Food or Feed Product

As discussed above—a milk clotting aspartic protease enzyme composition as described herein may be used according to the art—e.g. to make a milk based product of interest (such as e.g. a cheese product).

As discussed above—the fourth aspect of the invention relates to a method for making a food or feed product comprising adding an effective amount of a milk clotting aspartic protease enzyme composition of any of first or second aspect or any herein relevant embodiments thereof to the food or feed ingredient(s) and carrying out further manufacturing steps to obtain the food or feed product.

Preferably, the food or feed product is a milk based product and wherein the method comprises adding an effective amount of the isolated chymosin polypeptide variant as described herein to milk and carrying our further manufacturing steps to obtain the milk based product.

The milk may e.g. be sheep milk, goat milk, buffalo milk, yak milk, *lama* milk, camel milk or cow milk.

The milk based product may e.g. be a fermented milk product, a quark or a cheese.

It may be preferred that the method for making a food or feed product of the fourth aspect or herein relevant embodiments thereof is a method, wherein a milk clotting aspartic protease enzyme composition first have been stored according to the method for storage of a milk clotting aspartic protease enzyme of the third aspect and thereafter added to the food or feed ingredient(s) according to the method for making a food or feed product of the fourth aspect.

Fifth Aspect—a Process for Isolating a Milk Clotting Aspartic Protease Enzyme

As discussed above—the fifth aspect of the invention relates to a process for isolating a milk clotting aspartic protease enzyme of interest from an aqueous medium comprising such an enzyme of interest, wherein the method comprises the steps of:
- (i): obtaining an aqueous sample consisting of a number of components including the aspartic protease;
- (ii): adding polymer in a concentration from 1 ppm to 10000 ppm to the aqueous sample of step (i) to get a polymer containing sample; and
- (iii): isolating the aspartic protease from the polymer containing sample of step (ii) and thereby obtaining the isolated milk clotting aspartic protease enzyme of interest;

wherein the polymer is a polymer having the characteristics (a), (b) and (c) and optionally (D) of first aspect.

For the process of the fifth aspect—preferred examples/embodiments of milk clotting aspartic protease enzymes are described above.

For the process of the fifth aspect—preferred examples/embodiments of polymer are described above.

It is preferred that the polymer is added in step (ii) in a polymer concentration from 10 ppm to 5000 ppm (w/w), more preferably is in a concentration from 100 ppm to 4000 ppm (w/w) and even more preferably is in a concentration from 300 ppm to 3000 ppm (w/w).

The term "isolating" in step (iii) should be understood as the skilled person would understand it in the present context—i.e. that the obtained isolated milk clotting aspartic protease enzyme in step (iii) is more isolated (i.e. more pure) as compared to the aqueous sample consisting of a number of components including the aspartic protease of step (i).

As an example—the in step (iii) obtained isolated milk clotting aspartic protease enzyme may have a purity of e.g. at least 60% w/w of total protein (i.e. 60% w/w of total protein in the isolated composition is the isolated clotting aspartic protease enzyme). It may also be even more purified—i.e. at least 90% w/w of total protein.

Preferably, the polymer is Polyethylene glycol (PEG) Polyvinylpolypyrrolidone, Polyvinyl alcohol, Polyvinyl acetate, Polyacrylonitrile, Polyacrylate, Polymethacrylate or Brij35.

When the polymer is Polyethylene glycol (PEG) Polyvinylpolypyrrolidone, Polyvinyl alcohol, Polyvinyl acetate, Polyacrylonitrile, Polyacrylate or Polymethacrylate—it is preferred that the polymer is a polymer with a molecular mass from 1500 g/mol to 40000 g/mol, such as e.g. a polymer with a molecular mass from 2000 g/mol to 30000 g/mol or such as e.g. a polymer with a molecular mass from 5000 g/mol to 15000 g/mol.

Preferably the polymer is Polyethylene glycol (PEG) or Brij35.

In relation to PEG it may be preferred that the polymer is a polymer with a molecular mass from 1500 g/mol to 40000 g/mol, such as e.g. a polymer with a molecular mass from 2000 g/mol to 30000 g/mol or more preferred polymer with a molecular mass from 5000 g/mol to 15000 g/mol.

In a preferred embodiment—the in step (iii) isolated milk clotting aspartic protease enzyme is an enzyme which:
- has a specific activity of the milk clotting aspartic protease enzyme higher than 300 IMCU/mg total milk clotting aspartic protease enzyme protein, more preferably is the specific activity milk clotting aspartic protease enzyme higher than 350 IMCU/mg total milk clotting aspartic protease enzyme protein, wherein the milk clotting aspartic protease enzyme is *Camelius dromedarius* chymosin comprising the polypeptide amino acid sequence shown in FIG. 5 herein (termed "Camel_chymosin") or a variant of *Camelius dromedarius* chymosin, wherein the variant comprises a polypeptide sequence which has at least 90% (preferably at least 95%, more preferably at least 99%) sequence identity with the camel chymosin polypeptide amino acid sequence shown in FIG. 5 herein; or
- has a specific activity of the milk clotting aspartic protease enzyme higher than 150 IMCU/mg total milk clotting aspartic protease enzyme protein, more preferably is the specific activity milk clotting aspartic protease enzyme higher than 165 IMCU/mg total milk clotting aspartic protease enzyme protein, wherein the milk clotting aspartic protease enzyme is bovine chymosin comprising the polypeptide amino acid sequence shown in FIG. 5 herein (termed "Cow_chymosin") or a variant of bovine chymosin, wherein the variant comprises a polypeptide sequence which has at least 90% (preferably at least 95%, more preferably at least 99%) sequence identity with the bovine chymosin polypeptide amino acid sequence shown in FIG. 5 herein.

The aqueous sample consisting of a number of components including the aspartic protease of step (i) may be obtained by recombinant production of the milk clotting aspartic protease enzyme in a production host cell (e.g. an eukaryotic production host cell).

As known in the art—before further downstream purification of e.g. the enzyme of interest one normally removes/separates production host cells and other unwanted material in the fermentation media (by e.g. centrifugation and/or filtrating)—i.e. to get a sample comprising the enzyme of interest without too many unwanted components such as e.g. production host cells. As known in the art—this may sometimes be termed a non-purified first filtrate—this term may be used herein and it may be an example of a herein relevant aqueous sample consisting of a number of components including the aspartic protease of step (i).

WO02/36752A2 (Chr. Hansen) describes a recombinant method to produce *Camelius dromedarius* chymosin (Camel chymosin) using *Aspergillus* cells (preferably *Aspergillus niger*) as production host cells.

Accordingly, it may be preferred that the recombinant production host cell is an *Aspergillus* cell (preferably *Aspergillus niger*).

Mucorpepsin derived from *Rhizomucor miehei* may preferably be produced by use of *Rhizomucor miehei* as production host cell.

It may be preferred that the process of the fifth aspect relates to a process with the proviso that the process is not a process, wherein PEG and inorganic salt are added to the aqueous sample of step (i) so as to form a liquid-liquid (aqueous) two phase system and then recover/isolate the aspartic protease from the PEG phase.

As discussed above—U.S. Pat. No. 5,139,943 describes a method that may be seen as based on use of such a liquid-liquid (aqueous) two phase system.

In a preferred embodiment, the process of the fifth aspect is a process, wherein the isolating step (iii) comprises the following steps:
- (A): applying the polymer containing sample of step (ii) onto a solid phase comprising a solid base matrix containing ligands which comprise a hydrophobic part in order to obtain adsorption of the aspartic protease of interest to the ligand; and
- (B): eluting the aspartic protease of interest from the solid phase in order to recover the aspartic protease and thereby obtaining the purified isolated milk clotting aspartic protease enzyme of interest.

In a preferred embodiment, the process of the fifth aspect is a process, wherein the steps (i) to (iii) of first aspect comprise:
- (i): the aqueous sample consisting of a number of components including the aspartic protease of step (i) of the fifth aspect is applied onto a solid phase comprising a solid base matrix containing ligands which comprise a hydrophobic part in order to obtain adsorption of the aspartic protease of interest to the ligand;
- (ii): the addition of the polymer in step (ii) of the fifth aspect is addition to the elution buffer; and
- (iii): the isolating step (iii) of fifth aspect comprises eluting the aspartic protease of interest from the solid phase in order to recover the aspartic protease and thereby obtaining the purified isolated milk clotting aspartic protease enzyme of interest.

The two preferred embodiments immediately above—may be seen as relating to chromatography (e.g. column chromatography) isolation procedures. As such chromatography is well known to the skilled person are it is therefore not necessary to describe chromatography procedures as such in great details herein.

The term "solid base matrix" refers to the solid backbone material which contains reactive functionality permitting covalent attachment of the ligand to said backbone material. This term may herein also be referred to as solid support matrix.

As known in the art—the backbone material may be inorganic such as e. g. silica, or organic. Organic backbone materials which are useful herein include as examples cellulose and derivatives hereof, agarose, dextran, polymers such as e. g. polyacrylates, polystyrene, polyacrylamide, polymethacrylate, copolymers.

As known in the art—an example of a solid base matrix may be a so-called resin—as known in the art this term may be used in relation to ion-exchange chromatography (IEC).

As known in the art—the solid base matrix may preferably be particles—for instance solid base matrix may comprises particles with a particle size of less than 750 μm or particles with a particle size of less 100 μm.

Reactive functionalities of the solid support matrix permitting covalent attachment of the ligand group are well known in the art and include e. g. hydroxyl, carboxyl, thiol and amino.

As used herein, the term "ligand" refers to a hydrophobic part (alternatively termed group) and a spacer arm for covalently attaching the ligand to the solid base matrix. The spacer arm can be any group or substituent which is capable of covalently attaching the selected group/part to the solid base matrix. Such spacer arms are well known in the art and include e.g. alkylene groups, aromatic groups, alkylaromatic groups, amido groups, amino groups, urea groups, carbamate groups.

The aqueous load medium comprising enzyme of interest is contacted with the ligands as described herein under conditions permitting the enzyme of interest to bind/adsorb to the ligands. The skilled person knows how to adjust the conditions (e.g. adjust the pH such as in the range of 3-10 including the range of 4-8 and/or adjust the flow rate) in order to obtain proper adsorption of an enzyme of interest to a ligand of interest.

As such this step is a routine step for the skilled person to perform and the skilled person knows a number of different herein relevant ligands (see e.g. the review article: Yang et al, Journal of Chromatography A, 1218 (2011) 8813-8825).

The skilled person knows a number of herein relevant purification/separation techniques, wherein one applies a herein relevant medium comprising enzyme of interest onto a solid phase comprising a solid base matrix containing herein relevant ligands to obtain adsorption of the enzyme of interest to the ligand—for instance, by use of at least one purification technique selected from the group consisting of: chromatography, column chromatography, bed adsorption, expanded bed adsorption (EBA), batch adsorption, membrane adsorption and ion-exchange chromatography (IEC).

It may herein be preferred by use of expanded bed adsorption (EBA) purification technique.

All these purification techniques are very well known to the skilled person—accordingly it is routine work for the skilled person to properly bind an enzyme of interest to a specific suitable used ligand and properly perform eluting step to thereby obtain purified/isolated enzyme of interest.

Said in other words—it is routine work for the skilled person to identify suitable solvent, buffers etc. in order to get proper adsorption of the enzyme of interest to the ligand in and proper eluting the enzyme of interest to thereby obtain purified/isolated enzyme of interest.

Accordingly, it is not believed necessary to describe these steps in many details herein.

As known in the art—the term "chromatography" relates to a physical method of separation in which the components to be separated are distributed between two phases, one of which is termed stationary (stationary phase) while the other (the mobile phase) moves in a definite direction.

As known in the art—the term "column chromatography" relates to a separation technique in which the stationary bed is within a tube.

As known in the art—the term "expanded bed adsorption (EBA)" relates to a preparative chromatographic technique which makes processing of viscous and particulate liquids possible.

The protein binding principles in EBA are the same as in classical column chromatography and the common ion-exchange, hydrophobic interaction and affinity chromatography ligands can be used. Where classical column chromatography uses a solid phase made by a packed bed, EBA uses particles in a fluidized state. The EBA resin contains particles of varying size and density which results in a gradient of particle size when expanded and when the bed is in its expanded state, local loops are formed. Particles such as whole cells or cell debris, which may clog a packed bed column, readily pass through a fluidized bed. EBA can therefore be used on crude culture broths or slurries of broken cells, thereby bypassing initial clearing steps such as centrifugation and filtration, which is may be required when packed beds are used.

The terms "bed adsorption", "batch adsorption" and "membrane adsorption" are all well-known and clear to the skilled person in the present context.

As known in the art—a hydrophobic part of a ligand may e.g. be an aliphatic group or an aromatic group.

Aliphatic group may e.g. be an alkyl group with different lengths e.g. a $C_2$ to $C_{40}$ alkyl group or a $C_4$ to $C_{30}$ alkyl group;
an alkenyl group with different lengths e.g. a $C_2$ to $C_{40}$ alkenyl group or a $C_4$ to $C_{30}$ alkenyl group or e.g.
an alkynyl group with different lengths e.g. a $C_2$ to $C_{40}$ alkynyl group or a $C_4$ to $C_{40}$ alkynyl group.

Aromatic group may e.g. be a phenyl group or a benzyl group.

In a preferred embodiment the hydrophobic part of the ligand is a benzyl group.

In a preferred embodiment herein—the ligands also comprise a positively charged part—i.e. the ligands comprise a hydrophobic part and a positively charged part.

As known in the art—a positively charged part of a ligand may e.g. be an amino group or e.g. a quaternary ammonium group.

Preferably—the hydrophobic part is a benzyl group and the positively charged part is an amino group—i.e. the ligand is benzylamine.

EXAMPLES

Example 1: Determination of Specific Milk-Clotting Activity 4.1 Determination of Clotting Activity Milk clotting activity was determined using the REMCAT method, which is the standard method developed by the International Dairy Federation (IDF method)

Milk clotting activity is determined from the time needed for a visible flocculation of a standard milk substrate prepared from a low-heat, low fat milk powder with a calcium chloride solution of 0.5 g per liter (pH 6.5). The clotting time of a milk-clotting enzyme sample is compared to that of a reference standard having known milk-clotting activity and having the same enzyme composition by IDF Standard 110B as the sample. Samples and reference standards were measured under identical chemical and physical conditions. Variant samples were adjusted to approximately 3 IMCU/ml using an 84 mM acetic acid pH 5.5 buffer. Hereafter, 200 µl enzyme was added to 10 ml preheated milk (32° C.) in a glass test tube placed in a water bath, capable of maintaining a constant temperature of 32° C.±1° C. under constant stirring.

The total milk-clotting activity (strength) of a milk-clotting enzyme is calculated in International Milk-Clotting Units (IMCU) per ml relative to a standard having the same enzyme composition as the sample according to the formula:

$$\text{Strength in } IMCU/ml = \frac{Sstandard \times Tstandard \times Dsample}{Dstandard \times Tsample}$$

| | |
|---|---|
| Sstandard: | The milk-clotting activity of the international reference standard for rennet. |
| Tstandard: | Clotting time in seconds obtained for the standard dilution. |
| Dsample: | Dilution factor for the sample |
| Dstandard: | Dilution factor for the standard |
| Tsample: | Clotting time in seconds obtained for the diluted rennet sample from addition of enzyme to time of flocculation |

4.2 Determination of Total Protein Content

Total protein content was determined using the Pierce BCA Protein Assay Kit from Thermo Scientific following the instructions of the providers.

4.3 Calculation of Specific Clotting Activity

Specific clotting activity (IMCU/mg total protein) was determined by dividing the clotting activity (IMCU/ml) by the total protein content (mg total protein per ml).

Example 2: Adding PEG or Brij-35 to Elution Buffer

Bovine chymosin or camel chymosin were recombinantly expressed in *Aspergillus niger* (roughly as described in WO02/36752A2).

The enzymes were purified by a solid phase extraction approach employing a benzylamine ligand covalently bound to agarose (similar to benzylamine ligand described in WO01/58924A2).

A 96 well filter plate equipped with a 25 µm PE filter and a well volume of 2 ml was packed with Fastline 1300 from Upfront Chromatography, Denmark.

Wells were packed with resin to give a bed height of 6-8 mm in all wells. The resin in all wells was equilibrated with 5 ml of 20 mM sodium malonate pH 5.7.

Supernatant from cultivations was adjusted to pH 5.7 by mixing 3 ml supernatant with 0.5 ml 2 M sodium malonate pH 5.7. The 3.5 ml sample was then filtered through a 8 µm filter to remove particles and loaded to 96 individual wells of the plate. After loading the resin was washed with 5 ml of 20 mM malonate, 500 mM NaCl buffer pH 5.7 and allowed to run almost dry. The resin was eluted with 500 µl aliquots of 20 mM malonic acid pH 2.5, 100 mM NaCl, 5% glycerol and collected in vials.

In some experiments PEG-8000 or Brij-35 was added to the elution buffer to a final concentration of 0.05-0.25 w/w %.

In other experiments PEG-8000 or Brij-35 was added to the sample before the enzymes were bound to the resin to a final concentration of 0.05-0.25 w/w %.

In control experiments PEG-8000 or Brij-35 were not added.

Immediately after collection, 1.5 M di-sodium malonate was added to the eluate to adjust pH to 5.4-5.8.

Samples were analyzed for protein concentration and milk clotting activity within 1 day after isolation.

Protein concentration in collected fractions was analyzed using Pierce BCA Protein Assay Kit from Thermo Scientific.

Results:

FIG. 2A and FIG. 2B show the results of addition of 0.1% PEG8000 or Brij35 to the elution buffer as compared to control experiments without addition of PEG8000 or Brij35.

As can be seen in FIG. 2A and FIG. 2B—samples containing PEG8000 or Brij35 had two-fold increased specific activity over control sample purified without addition of PEG/Brij35.

Similar positive results were obtained in experiments were PEG-8000 or Brij-35 was added to the sample before the enzymes were bound to the resin.

Similar to FIG. 2A and FIG. 2B positive results were obtained by adding 0.05 w/w % PEG-8000 or Brij-35 or by adding 0.25 w/w % PEG-8000 or Brij-35.

Conclusions:

The results demonstrated that samples purified with addition of PEG8000 or Brij35 had two-fold increased specific activity over control sample purified without addition of PEG/Brij35.

It is believed that the eluate/samples contain PEG8000/Brij35.

Example 3: Adding PEG to Formulation (after Purification)

Liquid milk clotting aspartic protease enzyme composition comprising milk clotting aspartic protease enzyme at a strength of around 1100 IMCU/g were obtained.

Compositions were obtained for bovine chymosin, camel chymosin and mucor pepsin (i.e. 3 different compositions).

To each of the compositions were added PEG8000 to a content of 0.015% w/w (150 ppm w/w).

Control compositions were without addition of PEG8000.

The compositions were stored at 5° C. and 37° C. for 6 months and analyzed for milk clotting activity at regular intervals.

Results have demonstrated addition of PEG increased the longer term storage stability after 6 months storage of the tested liquid milk clotting aspartic protease enzyme compositions—i.e. these compositions had a higher IMCU/g activity.

Example 4: Adding PEG or Polysorbate 20 to Formulation (after Purification)

Liquid formulations of industrial enzymes are subjected to physical forces from unit operations such as pumping, stirring and filtration over membranes. During transportation of partly filled contained sloshing around of liquid formulation may also contribute to this. Shear stress and increased exposure of enzyme to the water-air interface may induce denaturation and concomitant loss of enzyme activity.

Physical stability of an enzyme or protein sample can be tested by repeatable shaking a sample in a test tube having high head space to sample volume ratio. The stability of different aspartic proteases towards shaking was investigated by inverting a 2 ml sample filled in a 10 ml tube in a rotary device for 1 hour. For each solution relative milk clotting activity was measured after 1 hour of vertical inversion and compared to a non-inverted control having the exact same composition. Results were expressed as "retained activity" which is obtained by diving activity of inverted sample with the activity of the non-inverted control sample.

Results:

PEG8000 added at a concentration of 0.015% (150 ppm) was found to have a remarkably protecting effect against shaking of all the tested aspartic proteases (Table x). The protecting effect of PEG800 was most profound for bovine chymosin and for camel chymosin were the loss in activity without PEG8000 added were 11% and 35%, respectively. When PEG8000 was added to samples of bovine chymosin and camel chymosin there was no loss in activity upon shaking of the samples. In samples of camel chymosin without PEG, a white precipitate was observed after shaking. There was no precipitate in samples of camel chymosin added PEG after shaking. This suggests that the loss in activity was due to protein aggregation upon denaturation and not surface adsorption of the enzyme to test tube surface. For mucor pepsin there was a minor protecting effect of PEG8000 on the physical stability.

The impact of PEG8000 on the stability of camel chymosin towards shaking was compared with the surfactants soya lecithin, polysorbate 20 and glycerol monostearate. From Table y it can be seen that the effect of polysorbate 20 was similar to the effect of PEG8000. The retained activity in samples of camel chymosin added either soy lecithin or glycerol monostearate was similar to the untreated control sample (no addition). This suggest that the stabilizing effect against shaking seen in this example is not due prevention of surface adsorption by surfactants, but a feature linked to the polyoxyethylene structural element contained in PEG8000 and Polysorbate 20.

TABLE x

Retained activity of samples of aspartic proteases subjected to shaking

| Enzyme | Addition of 0.015% PEG800 | Retained activity |
| --- | --- | --- |
| Bovine chymosin (CHY-MAX) | − | 89% |
|  | + | 101% |
| Camel chymosin (CHY-MAX M) | − | 65% |
|  | + | 100% |
| Mucor pepsin XL (Hannilase XP) | − | 96% |
|  | + | 98% |
| Mucor pepsin L (Hannilase L) | − | 97% |
|  | + | 102% |

TABLE y

Retained activity of camel chymosin samples subjected to shaking

| Compound | Retained activity |
| --- | --- |
| No addition | 76 (7) % |
| PEG (0.015%) | 98 (1) % |
| Soya lecithin (0.015%) | 73 (0) % |
| Soya lecithin (0.075%) | 69 (2) % |
| Polysorbate 20 (0.015%) | 100 (0) % |
| Polysorbate 20 (0.075%) | 100 (1) % |
| Glycerol monostearate (0.015%) | 75 (3) % |
| Glycerol monostearate (0.075%) | 71 (3) % |

Conclusions:

The results demonstrate that PEG8000 has stabilizing effect on aspartic proteases against physical forces resulting from shaking a liquid sample. Furthermore, it is shown that other compounds containing a polyoxyethylene structural element, such as polysorbate 20, have similar stabilizing effects.

REFERENCES

1: EP2333056A1 (DSM, date of fling Dec. 4, 2007)

2: WO2012/127005A1 (DSM)

3: U.S. Pat. No. 5,139,943 (Genencor, published Aug. 18, 1992)

4: U.S. Pat. No. 7,998,705B2 (Fujifilm, published Aug. 16, 2011)

5: US2011/0008846A1 (Qiagen)

The invention claimed is:

1. A dried granulated milk clotting aspartic protease enzyme composition comprising:
   (i) a milk clotting aspartic protease enzyme at a strength of from 25 International Milk-Clotting Units (IMCU)/g of the composition to 30000 IMCU/g of the composition, as determined by a relative milk-clotting activity test (REMCAT) using the milk-clotting activity of the international reference standard for rennet as a reference standard;
   (ii) a polymer at a concentration of from 1 ppm to 5000 ppm (w/w), and
   (iii) a salt;
   wherein the polymer has the following characteristics (a), (b) and (c):
   (a) the polymer is a polymer of at least one monomer selected from ethylene oxide, vinylpolypyrrolidone, vinyl alcohol, vinyl acetate, acrylonitrile, acrylate and methacrylate;
   (b) the polymer has a molecular mass of from 200 g/mol to 50000 g/mol; and
   (c) the polymer has a number of monomers ("n number") of from n=5 to n=1250; and
   wherein a suspension of the dried granulated composition in water has a pH of from 2 to 8.

2. The milk clotting aspartic protease enzyme composition of claim 1, wherein the polymer is selected from polyethylene glycol (PEG), polyvinylpolypyrrolidone, polyvinyl alcohol, polyvinyl acetate, polyacrylonitrile, polyacrylate, polymethacrylate, polysorbate, and Brij 35.

3. The milk clotting aspartic protease enzyme composition of claim 1, wherein the polymer is selected from polyethylene glycol (PEG) having a molecular mass from 5000 g/mol to 15000 g/mol, polysorbate 20, and Brij35.

4. The milk clotting aspartic protease enzyme composition of claim 1, wherein the polymer is a substituted polymer comprising one or more substituent compound(s) different from the monomers of characteristic (a) and the molecular mass of the substituted polymer is within the range of characteristic (b) and the molecular mass of the substituent compound(s) is less than the molecular mass of the polymer part of the substituted polymer.

5. The milk clotting aspartic protease enzyme composition according to claim 1, wherein:
   the composition comprises the milk clotting aspartic protease enzyme at a strength of from 100 IMCU/g of the composition to 10000 IMCU/g of the composition;
   the composition comprises the polymer at a concentration of from 100 ppm to 3000 ppm (w/w);
   the salt is selected from NaCl, KCl, $Na_2SO_4$, $(NH_4)_2SO_4$, $K_2HPO_4$, $KH_2PO_4$, $Na_2HPO_4$, $NaH_2PO_4$, and combinations thereof;
   the milk clotting aspartic protease enzyme is selected from:
   *Camelius dromedarius* chymosin comprising the Camel chymosin amino acid sequence set forth in FIG. 5 (SEQ ID NO:5) or a variant thereof, wherein the variant comprises an amino acid sequence which has at least 90% sequence identity with the Camel_chymosin amino acid sequence set forth in FIG. 5 (SEQ ID NO:5), wherein the specific activity of the milk clotting aspartic protease enzyme is higher than 300 IMCU/mg total milk clotting aspartic protease enzyme protein, and
   bovine pepsin comprising the Cow pepsin amino acid sequence set forth in FIG. 5 (SEQ ID NO:7) or a variant thereof, wherein the variant comprises an amino acid sequence which has at least 90% sequence identity with the Cow pepsin amino acid sequence set forth in FIG. 5 (SEQ ID NO:7), wherein the specific activity of the milk clotting aspartic protease enzyme is higher than 150 IMCU/mg total milk clotting aspartic protease enzyme protein; and
   the dried granulated composition has a total weight of from 0.5 g to 50 kg.

6. A method for storing a milk clotting aspartic protease enzyme, comprising storing a milk clotting aspartic protease enzyme composition of claim 1 for a period from 90 days to 2000 days at a temperature from −10° C. to 50° C.

7. A method for making a milk-based food or feed product comprising adding an effective amount of a milk clotting aspartic protease enzyme composition of claim 1 to milk and carrying out further manufacturing steps to obtain the milk-based food or feed product,
   wherein the milk is selected from sheep milk, goat milk, buffalo milk, yak milk, lama milk, camel milk and cow milk; and
   wherein the milk-based product is selected from a fermented milk product, a quark and a cheese.

8. The method of claim 7, further comprising, prior to said adding, storing said milk clotting aspartic protease enzyme composition for a period from 90 days to 2000 days at a temperature from −10° C. to 50° C.

* * * * *